United States Patent
Weldon et al.

(10) Patent No.: US 12,290,238 B2
(45) Date of Patent: May 6, 2025

(54) ADJUSTABLE STIFFNESS MEDICAL DEVICES

(71) Applicant: Boston Scientific Scimed, Inc., Maple Grove, MN (US)

(72) Inventors: James Weldon, Newton, MA (US); Scott E. Brechbiel, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 779 days.

(21) Appl. No.: 17/488,366

(22) Filed: Sep. 29, 2021

(65) Prior Publication Data

US 2022/0095893 A1    Mar. 31, 2022

Related U.S. Application Data

(60) Provisional application No. 63/085,323, filed on Sep. 30, 2020.

(51) Int. Cl.
*A61B 1/005* (2006.01)
*A61B 1/00* (2006.01)
*A61M 25/00* (2006.01)
*A61M 25/01* (2006.01)

(52) U.S. Cl.
CPC ........ *A61B 1/0057* (2013.01); *A61B 1/00078* (2013.01); *A61B 1/0052* (2013.01); *A61M 25/0054* (2013.01); *A61M 25/0136* (2013.01); *A61M 25/0147* (2013.01)

(58) Field of Classification Search
CPC . A61B 1/0057; A61B 1/00078; A61B 1/0052; A61B 1/00042; A61B 1/00066; A61M 25/0054; A61M 25/0136; A61M 25/0147
See application file for complete search history.

(56) References Cited

U.S. PATENT DOCUMENTS

| | | | |
|---|---|---|---|
| 2008/0208139 A1* | 8/2008 | Scheurer | A61M 5/158 604/192 |
| 2015/0087905 A1* | 3/2015 | Ueda | A61B 1/0057 604/95.04 |
| 2017/0127910 A1 | 5/2017 | Asaoka et al. | |

FOREIGN PATENT DOCUMENTS

| | | |
|---|---|---|
| JP | 2002360504 A | 12/2002 |
| JP | 2012081011 A | 4/2012 |

OTHER PUBLICATIONS

International Search Report and Written Opinion issued in International Application No. PCT/US2021/052496, issued Jan. 11, 2022 (60 pages).

* cited by examiner

*Primary Examiner* — Nathan R Price
*Assistant Examiner* — Haden Matthew Ritchie
(74) *Attorney, Agent, or Firm* — Bookoff McAndrews, PLLC

(57) ABSTRACT

A medical device may include: a shaft configured to be inserted into a body lumen of a subject; a handle at a proximal end of the shaft, the handle including an adjustment mechanism configured to be transitioned from a first configuration, in which the shaft has a first stiffness, to a second configuration, in which the shaft has a second stiffness. The first stiffness may be different from the second stiffness.

20 Claims, 15 Drawing Sheets

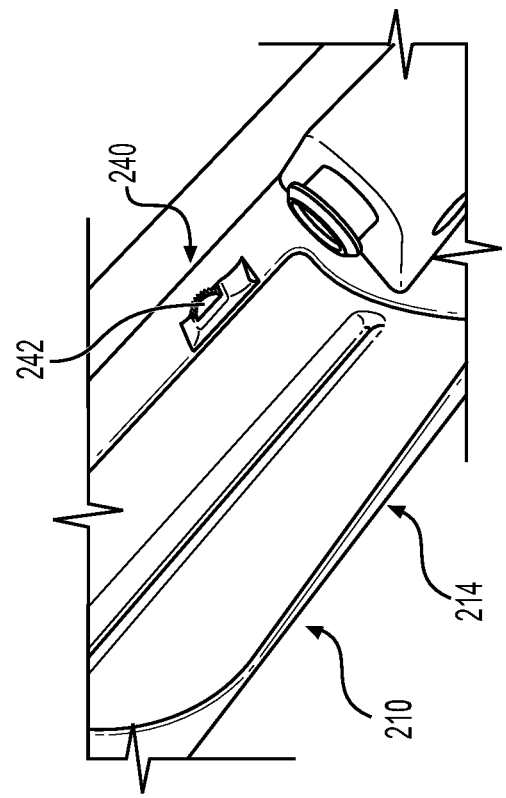
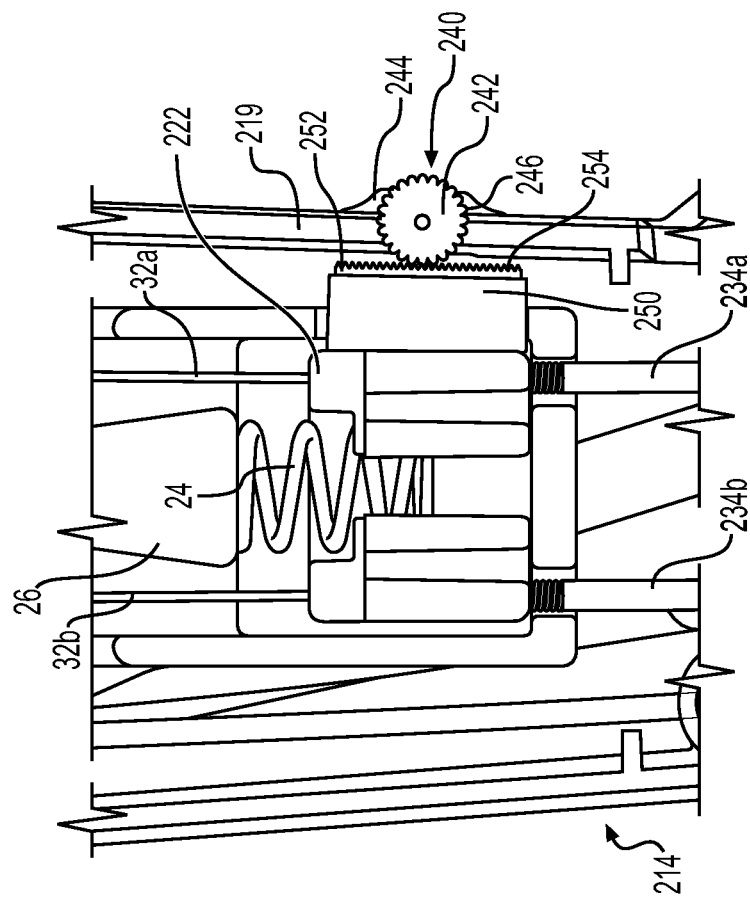
FIG. 4B
FIG. 4A

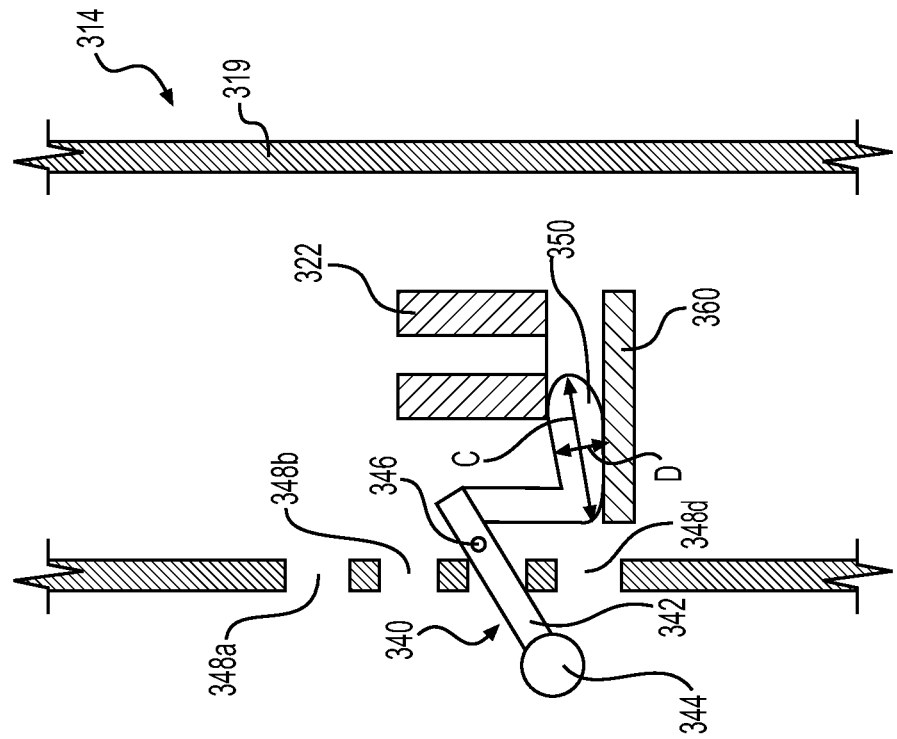
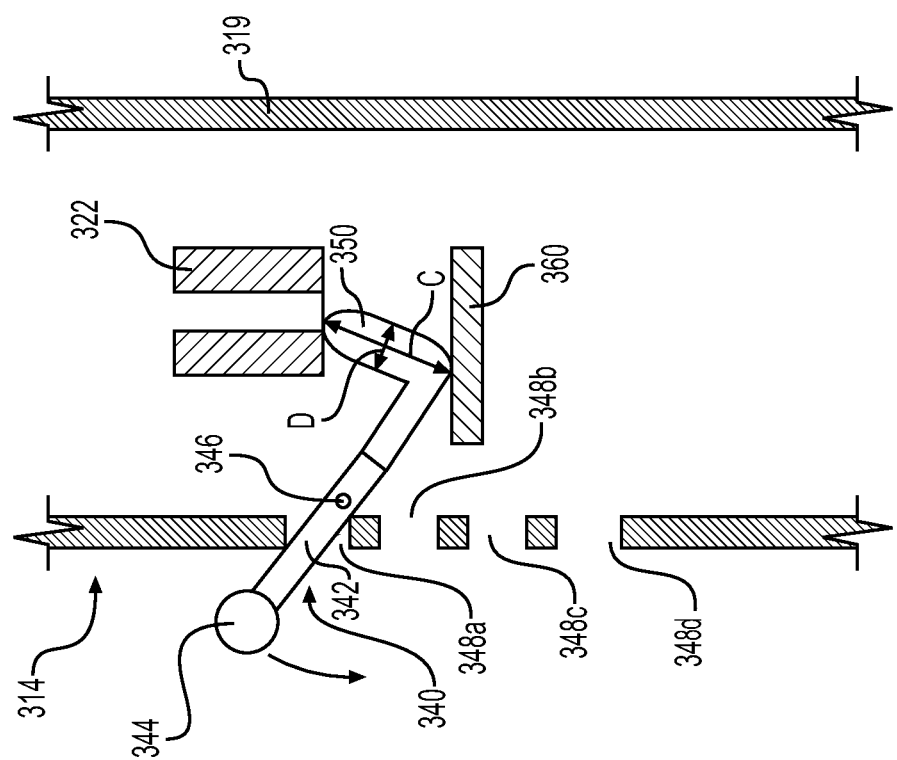

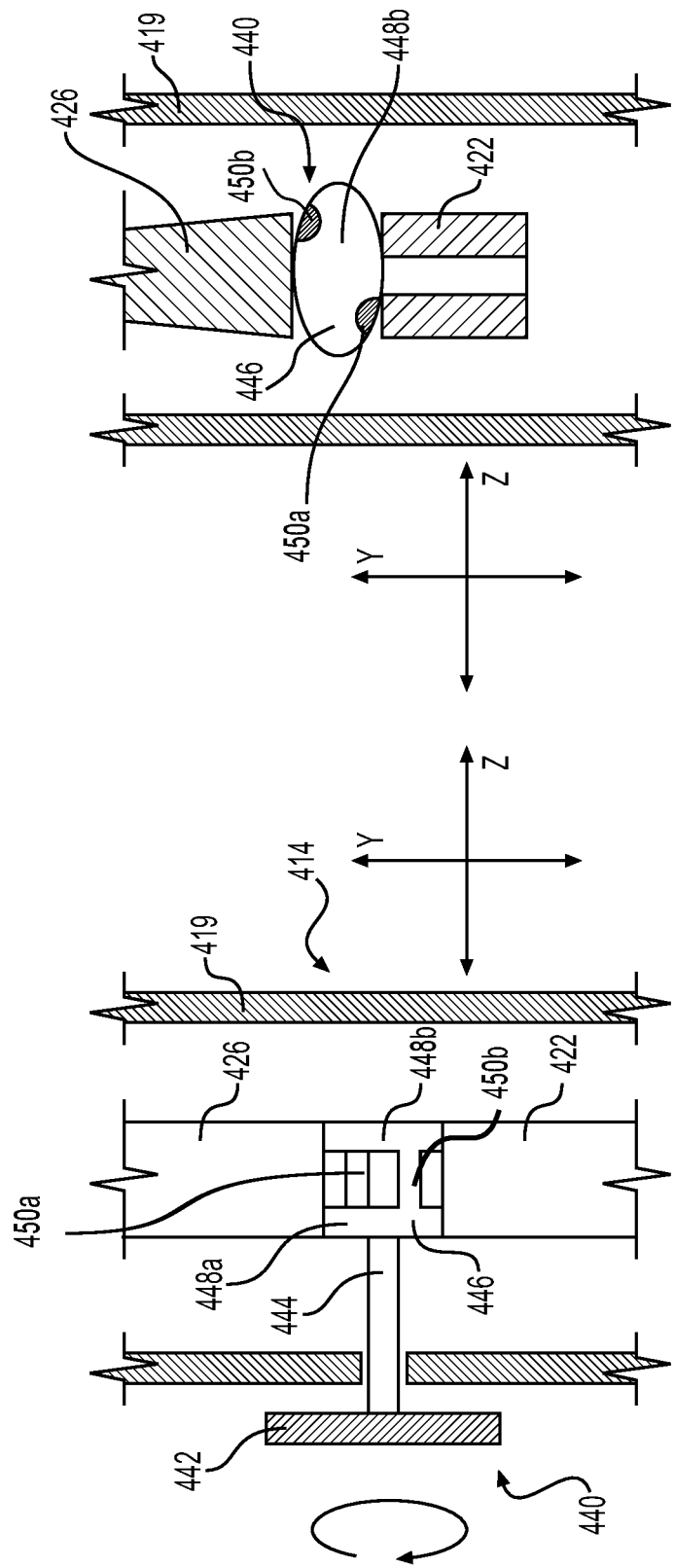

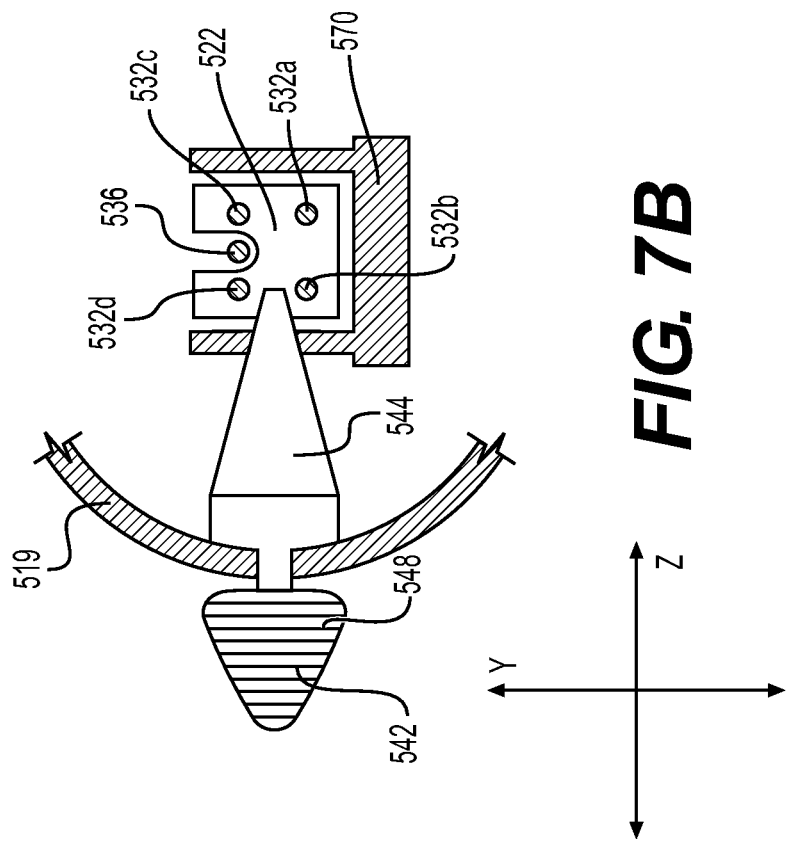
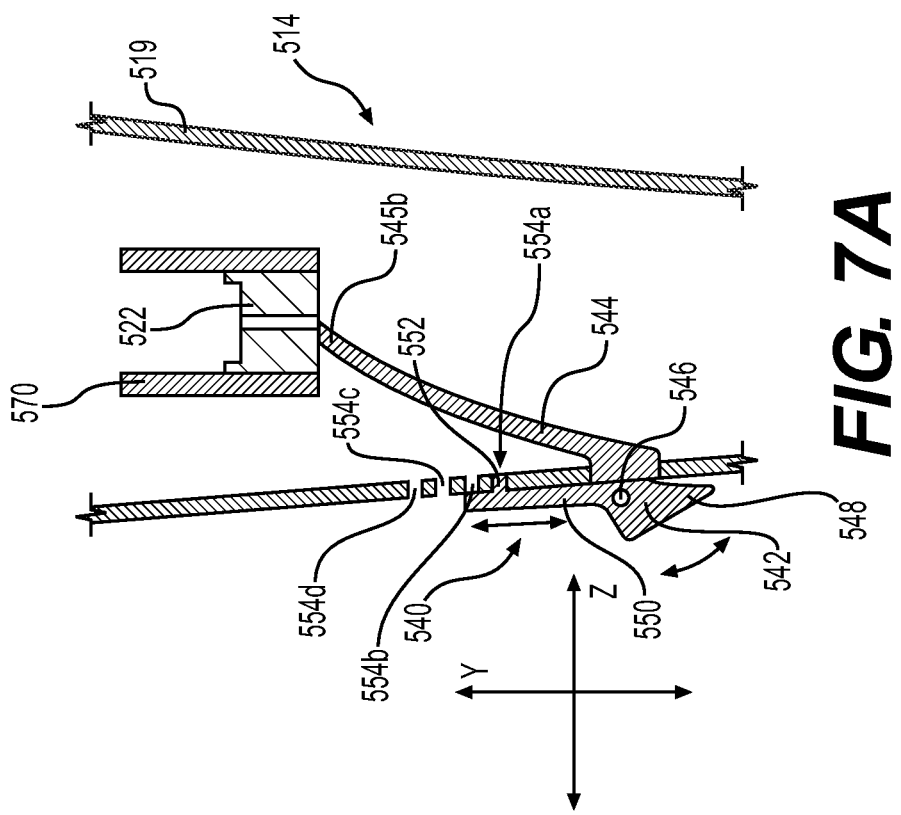
FIG. 7B
FIG. 7A

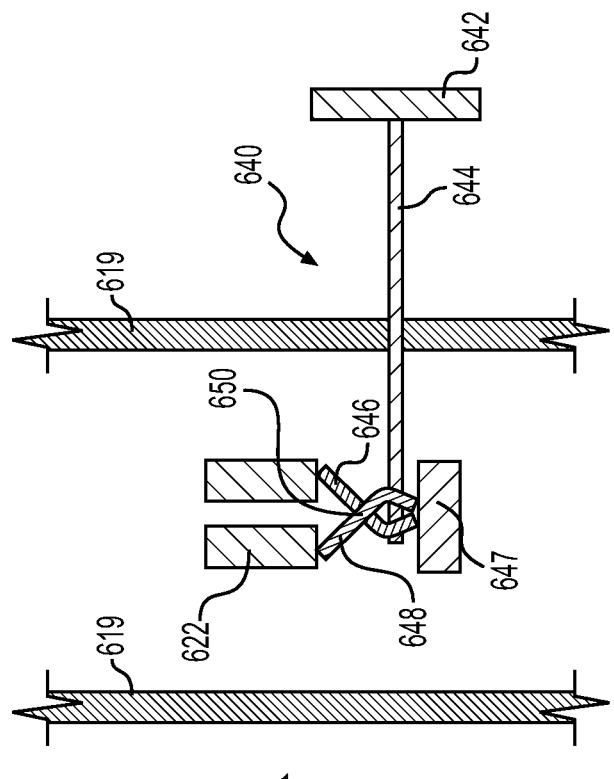
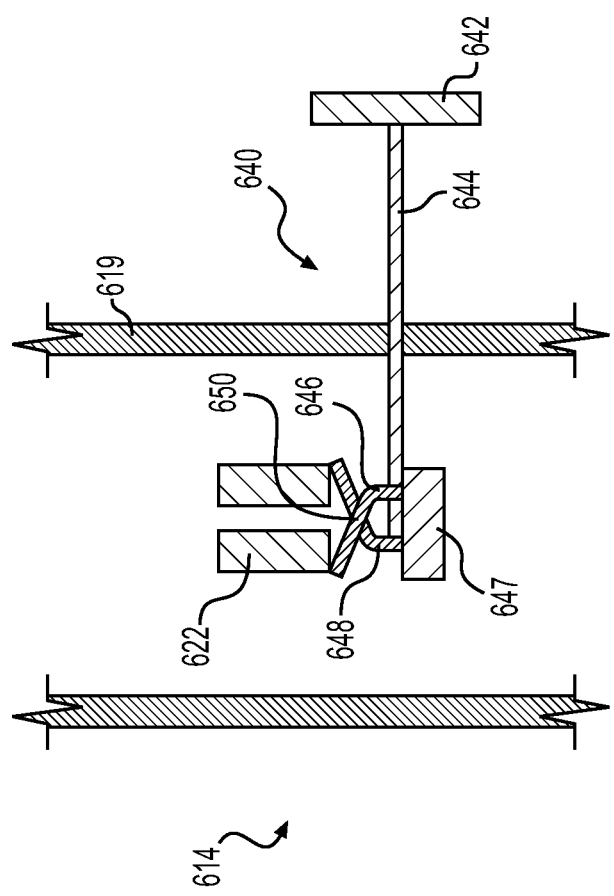

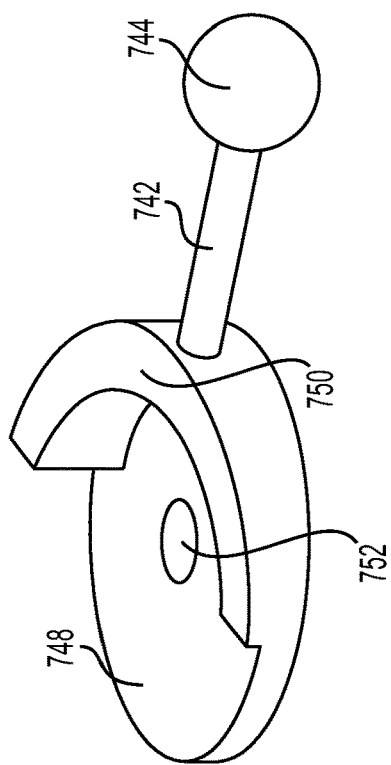
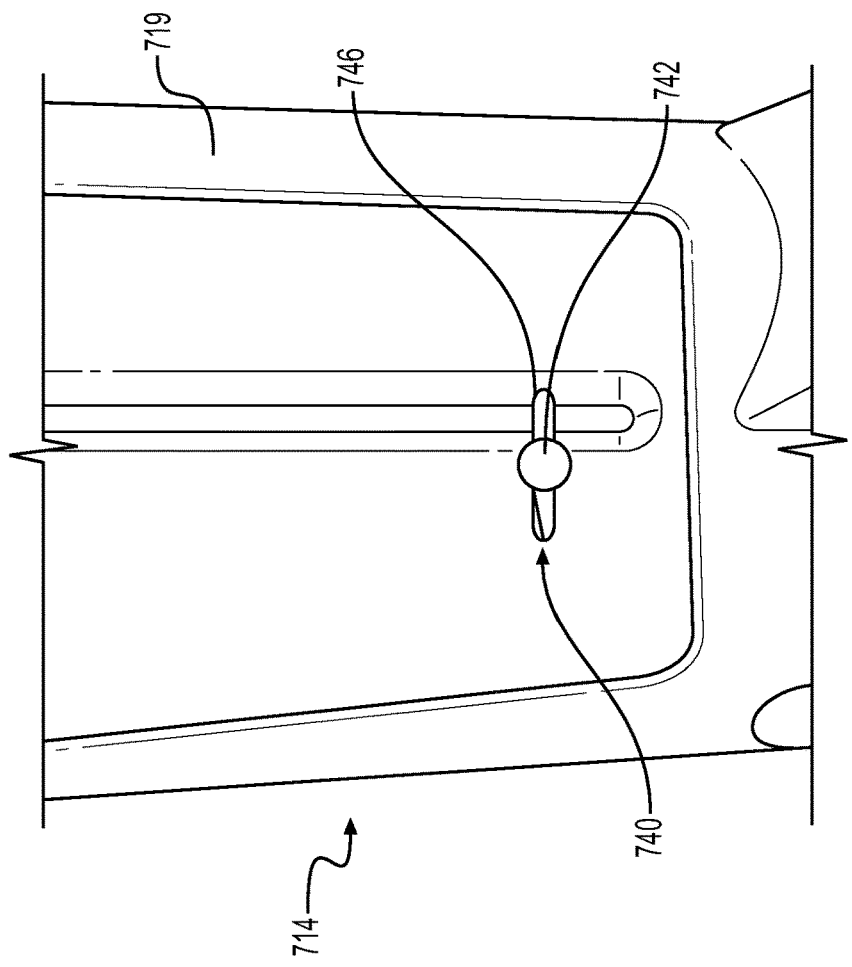
FIG. 9B
FIG. 9A

ADJUSTABLE STIFFNESS MEDICAL DEVICES

CROSS-REFERENCE TO RELATED APPLICATIONS

This patent application claims the benefit of priority under 35 U.S.C. § 119 to U.S. Provisional Patent Application No. 63/085,323, filed Sep. 30, 2020, which is herein incorporated by reference in its entirety.

TECHNICAL FIELD

This disclosure relates generally to devices and systems for adjusting stiffness of a medical device. In particular, this disclosure is directed to mechanisms for adjusting stiffness of insertion portions of medical devices.

BACKGROUND

Medical devices may include shafts that are insertable into a body of a subject. For example, the shafts may be insertable into a body lumen. The shafts may be steerable by an operator via a control mechanism. Such control mechanisms may be used to, for example, articulate the shaft of the medical device. The shafts may be flexible such that they may be bent without steering the shaft. In other words, the shafts may be bent passively during a procedure, as the shaft is inserted into the body lumen.

SUMMARY

In an example, medical device may include: a shaft configured to be inserted into a body lumen of a subject; and a handle at a proximal end of the shaft. The handle may include an adjustment mechanism configured to be transitioned from a first configuration, in which the shaft has a first stiffness, to a second configuration, in which the shaft has a second stiffness. The first stiffness may be different from the second stiffness.

Any of the devices or methods disclosed herein may have any of the following features. The handle may include: at least one Bowden cable having a Bowden sheath; and a body configured to exert a distal force on a proximal end of the Bowden sheath. The adjustment mechanism may be configured to change a position of the body relative to a housing of the handle. In transitioning from the first configuration to the second configuration, the body may be moved proximally. The adjustment mechanism may include a wheel. The wheel may include threads configured to interact with threads of the body in order to move the body proximally or distally. The body may include at least a central portion and an arm portion extending radially outward from the central portion. The threads of the body may be disposed on radially outer surfaces of the arm. The wheel may extend around a perimeter of the housing. The wheel may include teeth configured to interact with teeth of the body in order to move the body proximally or distally. The adjustment mechanism may include a cam. The cam may be positioned between the body and between a structure that is fixed relative to the housing. The cam may be movable via at least one of a lever or a rotatable knob. The adjustment mechanism may include a slidable lever and an arm extending radially inward into a cavity defined by the housing. An end of the arm may be configured to move the body proximally or distally. The adjustment mechanism may include a scissor lift. The shaft may include at least one control mechanism extending therethrough. The adjustment mechanism may be configured to change a force on the control mechanism. A first force may be exerted on the control mechanism in the first configuration and a second force may be exerted on the control mechanism in the second configuration. The first force may be greater than the second force.

In another example, a medical device may include a shaft configured to be inserted into a body lumen of a subject; and a handle at a proximal end of the shaft. The handle may include: at least one Bowden cable having a Bowden sheath; and a body configured to exert a distal force on the Bowden sheath, wherein the body is configured to be selectively moved in a proximal direction and a distal direction to change an amount of the distal force.

Any of the devices or methods described herein may include any of the following features. The handle may further include an adjustment mechanism configured to selectively move the body proximally or distally. The adjustment mechanism may include at least one of a wheel, a lever, a knob, or a slide. The adjustment mechanism may include threads on a surface of the adjustment mechanism.

In another example, a medical method may comprise: inserting a shaft of a medical device into a body lumen of a subject; and activating an adjustment mechanism on a handle of the medical device in order to cause the shaft of the medical device to increase in flexibility.

Any of the devices or methods disclosed herein may include any of the following features. Activating the adjustment mechanism may cause a body to move proximally relative to a housing of the handle.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The terms "approximately" or "substantially" may be understood as referring to a range of +/−10%. As used herein, the term "proximal" means a direction closer to an operator and the term "distal" means a direction further from an operator. Although duodenoscopes are referenced herein, reference to duodenoscopes should not be construed as limiting the possible applications of the disclosed mechanisms and other aspects. For example, the disclosed aspects may be used with various types of endoscopes, bronchoscopes, gastroscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the disclosure and together with the description, serve to explain the principles of the disclosure.

FIGS. 3A-10D depict exemplary mechanisms for adjusting a flexibility of a shaft a duodenoscope, such as the duodenoscope of FIGS. 2A and 2B.

DETAILED DESCRIPTION

Handles of duodenoscopes or other medical devices (e.g., operational portions of duodenoscopes) may include components that are used by an operator when performing a procedure with the duodenoscope. The handle may be used to insert a shaft of a duodenoscope into a body lumen of the patient, actively steer a distal tip of the duodenoscope, guide the shaft such that it passively bends through a body lumen, or perform other functions. During different phases of a medical procedure, as discussed in greater detail below, it may be desirable for the shaft to have different stiffness levels. As described in this disclosure, various mechanisms may be used to allow for proximal and distal movement of internal parts of the handle of the duodenoscope, thereby adjusting a stiffness of the shaft of the duodenoscope. For example, the mechanism can translate a part connected to or otherwise contacting proximal ends of Bowden cable sheaths, thereby altering a stiffness of the duodenoscope shaft.

Figure 1A:
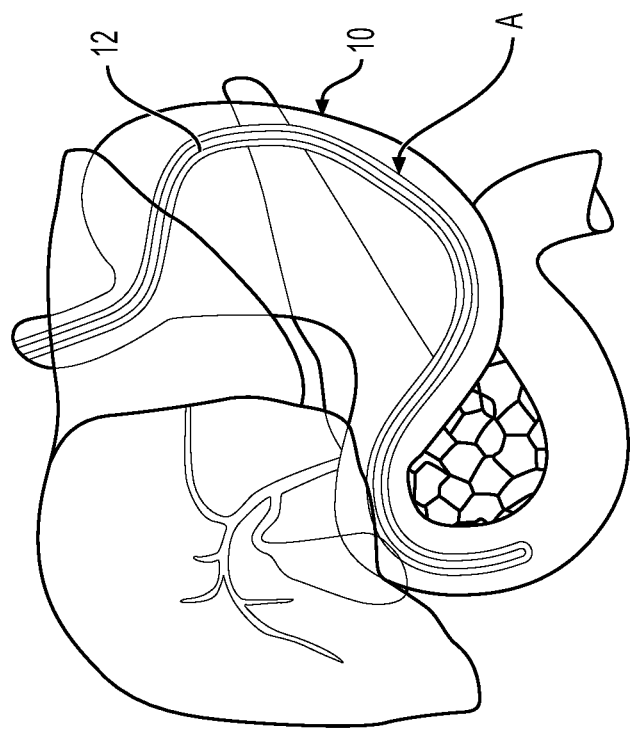
FIGS. 1A and 1B depict an exemplary medical procedure using a duodenoscope.
Figure 1B:
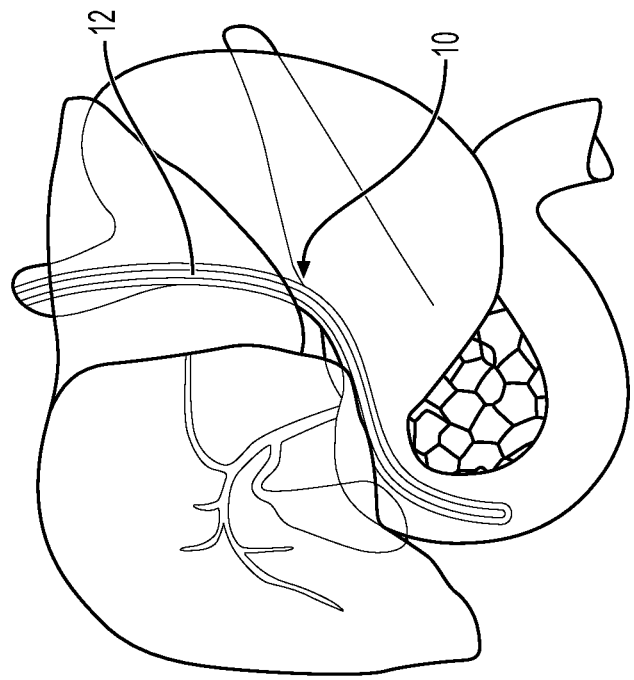

Referring now to the figures, FIGS. 1A and 1B depict aspects of a procedure using a duodenoscope 10. As shown in FIGS. 1A and 1B, a shaft 12 of duodenoscope 10 may be inserted into a gastrointestinal lumen of a subject. During a procedure such as an endoscopic retrograde cholangiopancreatography ("ERCP") procedure, an operator may navigate shaft 12 through an esophagus, through a greater curvature of the stomach, through a pylorus, and into a duodenum, in order to access a papilla. As shaft 12 is being navigated, shaft 12 may be in a long position, as shown in FIG. 1A, in which shaft 12 is more proximate to the greater curvature of the stomach than to a lesser curvature of the stomach.

After the operator reaches the duodenum of the subject, the operator may remove the gastric loop, indicated by reference letter A in FIG. 1A, to transition duodenoscope 10 to a short configuration, shown in FIG. 1B. As shown in FIG. 1B, in the short configuration, shaft 12 may be more proximate to the lesser curvature of the stomach than to the greater curvature of the stomach. Operators may prefer the short configuration of FIG. 1B after reaching the duodenum because shaft 12 is relatively straighter than in the long configuration of FIG. 1A and therefore more responsive to maneuvering (e.g., articulation of a distal end of shaft 12 and insertion of tools within a working channel of the duodenoscope).

However, it may be difficult to maintain a short position (FIG. 1B) of duodenoscope 10, because, a flexibility of shaft 12 may change, for example, as devices are passed through a working channel of shaft 12. The position of the duodenoscope also may change as a patient moves. This may result in shaft 12 falling out of the duodenum, back into the stomach. Furthermore, different operators may have different preferences regarding a stiffness of shaft 12. Operators may prefer a shaft 12 that is stiff enough to navigate and maintain position but flexible enough to reduce a risk of perforation. Therefore, it may be desirable for duodenoscope 10 to have features that allow a stiffness of shaft 12 to be adjustable.

Figure 2A:
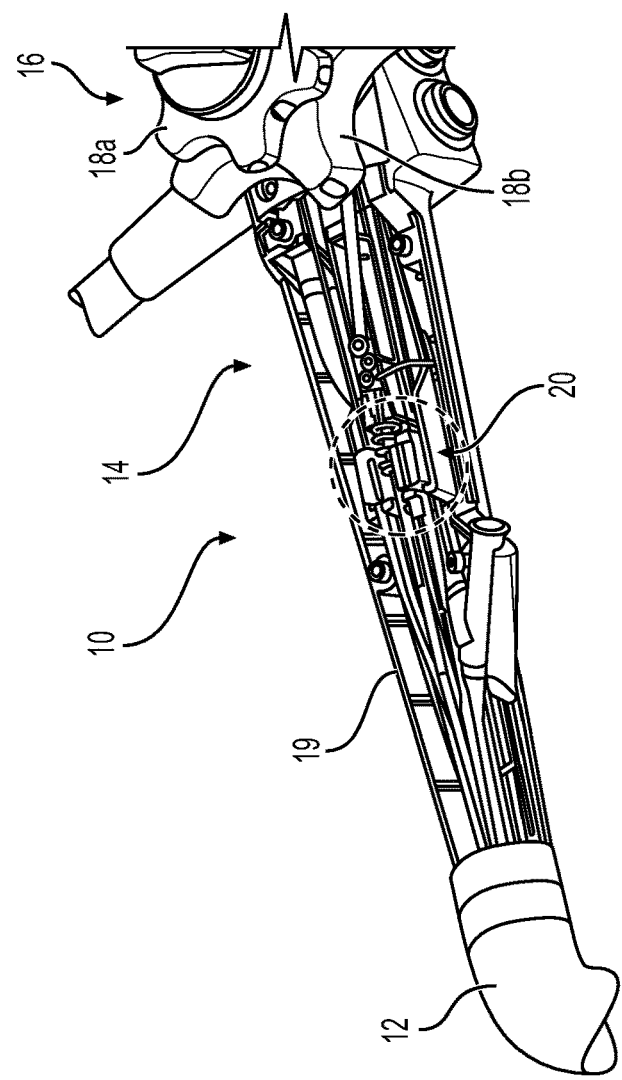
FIGS. 2A and 2B depict aspects of a duodenoscope, such as the duodenoscope used in FIGS. 1A and 1B.
Figure 2B:
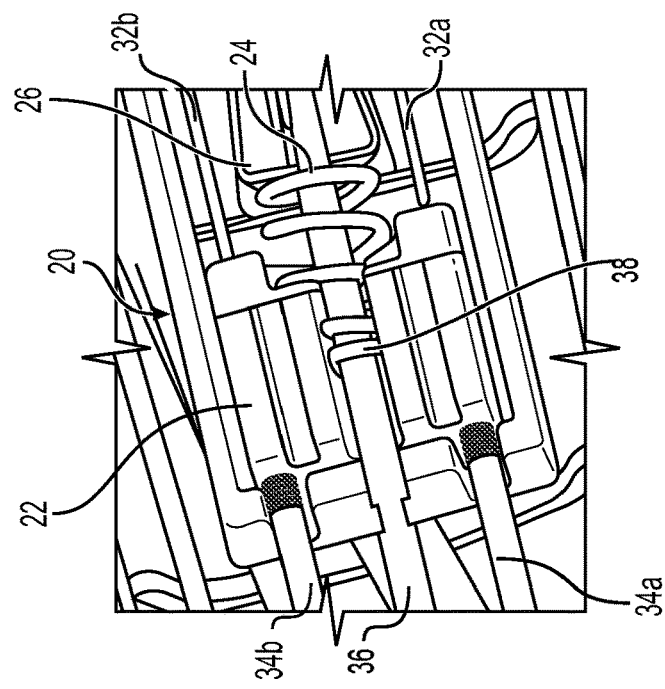

FIGS. 2A and 2B depict aspects of duodenoscope 10, including shaft 12 and a handle 14 of duodenoscope 10. FIG. 2B depicts in greater detail the portion of FIG. 1A in the dashed circle. Handle 14 may include a steering assembly 16, which may include knobs 18a and 18b. Knobs 18a and 18b may be operable to articulate a distal tip of shaft 12 in one or more directions. For example, one of knobs 18a and 18b may be used to articulate the distal tip in an up/down direction, and the other of knobs 18a and 18b may be used to articulate the distal tip in a left/right direction. Handle 14 may also include a housing 19 that encloses components of handle 14 and that defines a cavity.

A tension assembly 20 may be enclosed within housing 19. Tension assembly 20 may serve to align and provide tension to various components of handle 14/shaft 12. Tension assembly 20 may include a body such as a spring block 22. Spring block 22 may include passages (e.g., holes or grooves) for receiving steering elements or elements that control other portions of duodenoscope 10 (e.g., an elevator of duodenoscope 10).

A spring 24 may extend between spring block 22 and a distal-facing surface of a body 26 that is proximal of spring block 22. Spring 24 may exert a distal force on spring block 22, which may apply tension to steering components, as described below. Spring 24 may have, for example, a helical, cylindrical shape. Alternatively, spring 24 may have a cone/funnel shape, with a narrowest end of the helix extending into spring block 22, and with a widest end of the helix pressing against the distal-facing surface of body 26. Body 26 may be fixed relative to housing 19, facilitating the distal force of spring 24 on spring block 22. Spring 24 may be flush at a distal end of a housing of spring block 22.

Bowden cables 32a and 32b may extend distally from spools or other structures that are manipulated by knobs 18a and 18b. Although two Bowden cables 32a and 32b are visible in the cross-sectional view of FIG. 2B, it will be appreciated that additional Bowden cables may be present. For example, a total of four Bowden cables may be used. Each of the Bowden cables, including Bowden cables 32a, 32b, may be associated with a direction of movement of the distal tip of shaft 12 (e.g., up, down, left, or right). Bowden cables 32a and 32b (and other Bowden cables of handle 14) may pass through, and translate within, spring block 22, which may serve to maintain Bowden cables 32a and 32b (and other Bowden cables) approximately parallel to one another.

Distally of spring block 22, Bowden sheaths 34a and 34b may encircle or otherwise encompass Bowden cables 32a and 32b, respectively. Other Bowden sheaths (not visible in the cross-sectional view of FIG. 2B) may encircle other Bowden cables. For example, duodenoscope 10 may include four Bowden sheaths. Bowden cables 32a, 32b may translate relative to Bowden sheaths 34a, 34b. Bowden sheaths 34a, 34b may maintain tension in Bowden cables 32a, 32b by inhibiting Bowden cables 32a, 32b from changing lengths. Bowden sheaths 34a, 34b (and other Bowden sheaths), along with Bowden cables 32a, 32b therein (and other Bowden cables within the other Bowden sheaths) may extend distally through shaft 12, toward a distal end of shaft 12, to facilitate articulation of shaft 12. For example, Bowden cables 32a and 32b may be fixed at their distal ends to a portion of an articulation joint (e.g., a distal end of the articulation joint). Distal ends of Bowden sheaths 34a and 34b may be fixed proximally of the distal ends of Bowden cables 32a and 32b. Alternatively, distal ends of Bowden sheaths 34a and 34b may abut a proximal-facing surface in a distal end of shaft 12, proximal of the distal ends of Bowden cables 32a and 32b, such that the distal ends of Bowden sheaths 34a and 34b are retained in a fixed position.

A distally-facing surface of spring block 22 may abut proximal ends of Bowden sheaths 34a and 34b (and other Bowden sheaths). Alternatively, proximal ends of Bowden sheaths 34a and 34b may be fixed to or within spring block 32, in a manner so that Bowden sheaths 34a and 34b receive Bowden cables 32a and 32b, respectively. Thus, the distal force on spring block 22 from spring 24 may exert a distal force on Bowden sheaths 34a and 34b (as well as other Bowden sheaths of handle 14). Spring block 22 may thus apply tension to Bowden sheaths 34a and 34b.

An amount of force exerted by spring block 22 on Bowden sheaths 34a and 34b (and other Bowden sheaths of handle 14) may affect a rigidity of shaft 12. A greater force on Bowden sheaths 34a and 34b (and other Bowden sheaths of handle 14) may result in a relatively greater stiffness of shaft 12.

An elevator control in a hypotube 36 may also pass through spring block 22. The control wire may be moved proximally and distally via a control mechanism (not shown) in order to raise and lower the elevator of duodenoscope 10. Hypotube 36 may pass through a center of spring block 36. Hypotube 36 may include a ridge 38 extending radially outward from control wire 36. Ridge 42 may limit a distal end of spring 24 from passing ridge 38, such that spring 24 is retained between ridge 38 and the distally-facing surface of body 26.

FIGS. 3A-10D depict mechanisms for allowing adjustment of a flexibility of shaft 12 by adjusting a position of a mechanism/part within a handle, such as spring block 22. A relatively more proximal position of spring block 22 may result in a smaller force of spring block 22 on Bowden sheaths 34a and 34b (and other Bowden sheaths of duodenoscope 10). The smaller force may result in less tension of Bowden sheaths 34a and 34b (and other Bowden sheaths of duodenoscope 10) and greater flexibility of shaft 12. The greater flexibility of shaft 12 may result in greater passive flexibility of shaft 12, and may also facilitate steering with a less responsive distal tip of shaft 12.

FIGS. 3A-10D may not depict all of the elements of duodenoscope 10 (including elements of handle 14). It will be appreciated that the features of duodenoscope 10 may be used along with the mechanisms of FIGS. 3A-10D. Where the mechanisms of FIGS. 3A-10D include elements that differ from the features of duodenoscope 10, the description below explains those differences. In all other circumstances, the mechanisms of FIGS. 3A-10D may be used along with a duodenoscope having features of duodenoscope 10. Like reference numbers are used below to indicate like structures, where feasible.

Figures 3A, 3B:
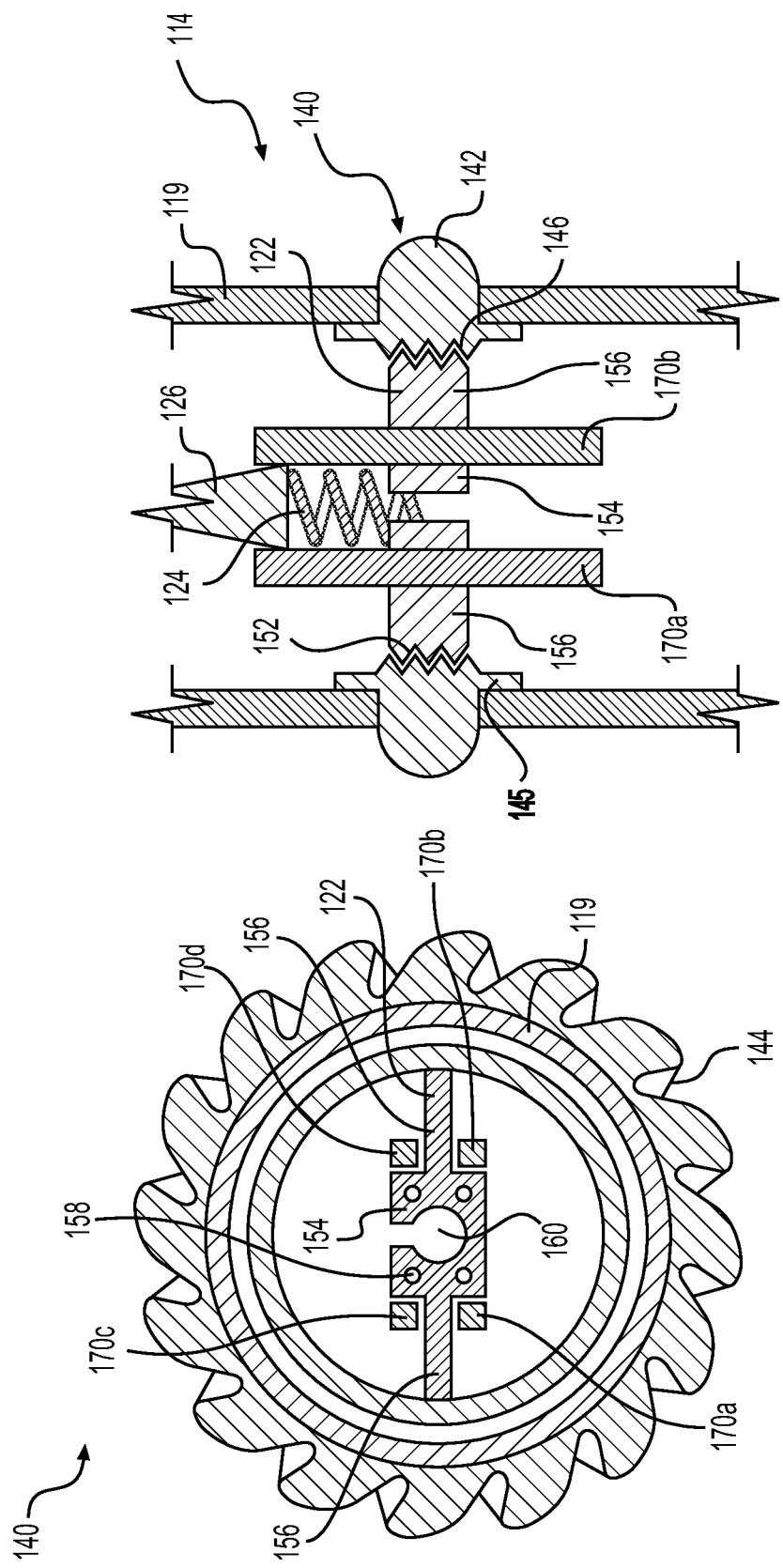
Figure 3D:
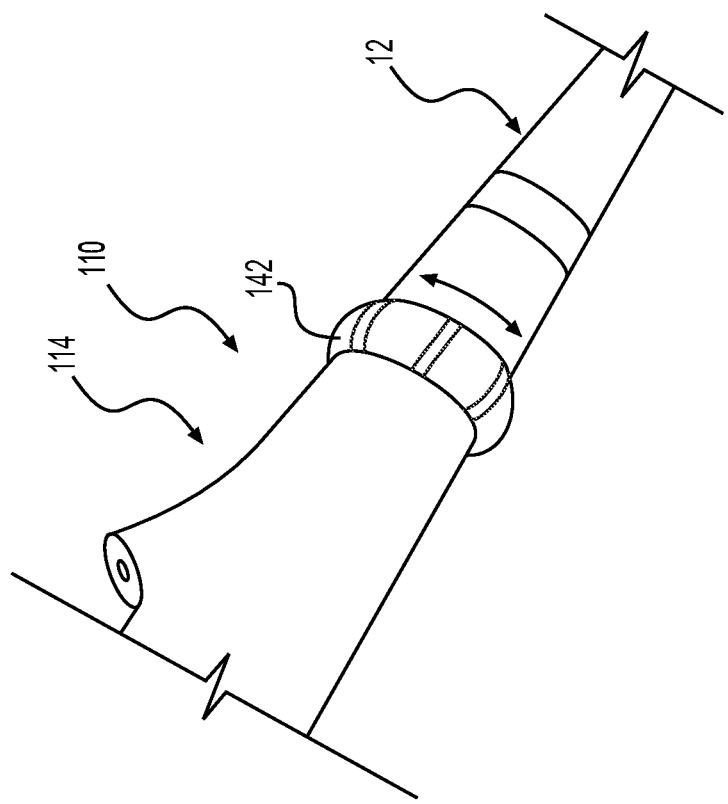
Figure 3C:
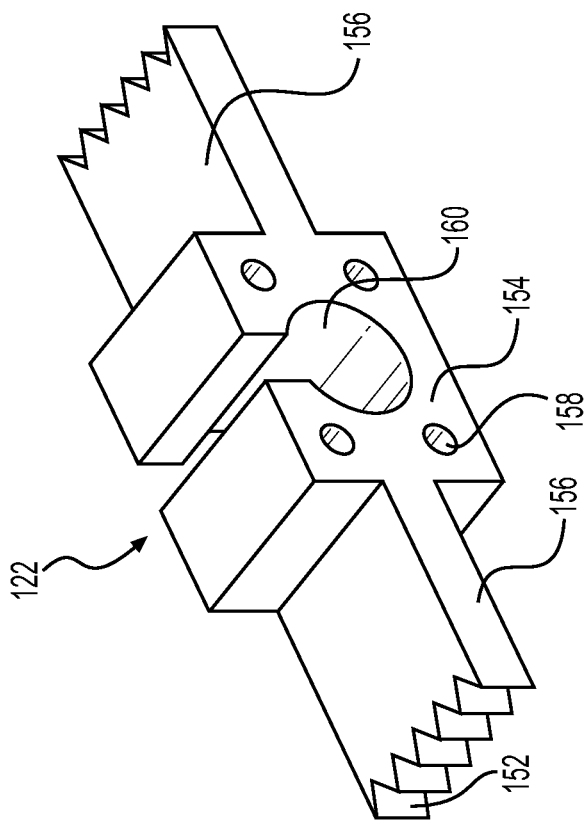

FIGS. 3A-3D depict an exemplary adjustment mechanism 140 for use with a duodenoscope 110 having a handle 114 and a shaft 12. FIG. 3A shows a proximal-facing cross-sectional view of handle 114. FIG. 3B shows a cross-sectional view of a portion of handle 114 along a central longitudinal axis of handle 114. FIG. 3C shows a perspective view of a spring block 122 used with adjustment mechanism 140. FIG. 3D shows a perspective view of handle 114. The views of FIGS. 3A-3D do not depict components such as Bowden cables, Bowden sheaths, or an elevator wire for simplicity of illustration. Those components may be used with the aspects described in FIG. 3A-3D, in the manner described with respect to duodenoscope 10.

Handle 114 (FIG. 3D) may include a housing 119 having any of the properties of housing 19, described above. A rotatable wheel 142 may extend radially around a perimeter of housing 119. Rotatable wheel 142 may be rotatable about a central longitudinal axis of rotatable wheel 142. The central longitudinal axis of rotatable wheel 142 may be coaxial with or approximately parallel to a central longitudinal axis of handle 114 at a longitudinal portion of handle 114 at which wheel 142 is disposed. Wheel 142 may extend through an opening extending about a circumference of housing 119. Wheel 142 may include grooves 144 (or protrusions) for increasing grip of a user and facilitating rotation of wheel 142 by a hand of a user. Wheel 142 may also include protrusions 145 for engaging with an inner surface of housing 119 and limiting wheel 142 from moving radially inward or outward with respect to housing 119. Thus, when a user presses on wheel 142, a portion of wheel 142 contacted by the user does not slip laterally/move radially inward.

A radially inward-facing surface of wheel 142 (or a radially inward-facing surface of another component fixed to wheel 142) may include wheel threads 146, which may extend helically around the radially inward-facing surface of wheel 142.

Wheel threads 146 of wheel 142 may interact with spring block threads 152 of spring block 122. Spring block 122 may have any of the features of spring block 22, described above, unless otherwise specified. Spring block 122 may include a central portion 154 and arms 156. Arms 156 may extend radially outward from central portion 154. Although two arms 156 are depicted in FIGS. 3A-3D, it will be appreciated that other numbers (e.g., more) arms may be used. Alternatively, arms 156 may be omitted and a disc or other shaped structure may extend radially outward to walls of housing 119 from central portion 154. Central portion 154 may have a substantially rectangular prism shape, not including cutouts described below. Arms 156 may also have a rectangular prism shape but may be thinner than central portion 154. Threads 152 may be at radially outward surfaces of arms 156.

Spring block 122 may include openings 158 for receiving Bowden cables (like Bowden cables 32a and 32b). As shown in FIGS. 3A and 3C, spring block 122 may include four longitudinally-extending openings 158 for receiving four respective Bowden cables. Alternative numbers of openings and respective Bowden cables may also be used. Spring block 122 may also include a central longitudinally-extending opening 160 for receiving an elevator wire (and, for example, hypotube 40) and a spring 124, which may extend around the elevator wire. Central opening 160 may be open to a radially outer surface of spring block 122 in order to facilitate positioning of the elevator wire or spring 124.

Spring 124 may extend between a distally-facing surface of a body 126 (having any of the properties of body 26) and spring block 122, as described above for spring block 22, spring 24, and body 26. Spring 124 may exert a distal force on spring block 122 and thus on Bowden sheaths distal to spring block 122.

Guide rails 170a, 170b, 170c, and 170d may extend longitudinally along outer surfaces of central portion 154, near a junction with arms 156. Arms 156 may join with central portion 154 such that four concave corners are formed where central portion 154 joins arms 156. Guide rails 170a, 170b, 170c, 170d may have surfaces with shapes complementary to a junction between central portion 154 and arms 156. For example, as shown in FIG. 3A, guide rails 170a, 170b, 170c, 170d may have square or rectangular cross sections that complement the corners formed at junctions of arms 156 and central portion 154. Although four guide rails 170a, 170b, 170c, 170d are described above, it will be appreciated that alternate numbers of guide rails may be used. For example, guide rails 170b and 170c may be omitted. Alternatively, based on a configuration of central portion 154 and arms 156, greater numbers of guide rails may be used. Guide rails 170a, 170b, 170c, 170d may be fixed to housing 19 or to another component within housing 19 that is fixed relative to housing 19. Guide rails 170a, 170b, 170c, 170d may be integral with housing 19 (e.g., of a single, unitary piece), and spring block 122 may include slots for receiving guide rails 170a, 170b, 170c, 170d.

As wheel 142 is rotated relative to housing 119, threads 146 of wheel 142 may interact with threads 152 of spring block 122 (e.g., of arms 156). However, guide rails 170a, 170b, 170c, 170d may prevent rotation of spring block 122 relative to housing 119. Thus, rotation of wheel 142 may cause spring block 122 to move proximally or distally. When wheel 142 is rotated in a first direction, spring block 122 may move distally. When wheel 142 is moved in a second direction, spring block 122 may move proximally.

A size of wheel 142/spring block 122 and a number and size of threads 146, 152 may be chosen to provide a desired amount, and degree of control e.g., fine) of proximal and/or distal movement of spring block 122. Wheel 142 and/or housing 119 may include index markers to indicate how far wheel 142 has been rotated and to thus indicate an amount of longitudinal movement of spring block 122. One or more of wheel 142, spring block 122 (e.g., arm 156), or housing 119 may limit movement of proximal or distal movement of wheel 142. Proximal movement of spring block 122 may be limited by body 126. Additionally or alternatively, housing 119 may include structures for receiving and limiting movement of spring block 122. For example, housing 119 may include protruding surfaces to limit proximal and/or distal movement of spring block 122. Slots may be included in the structure of housing 119 receiving spring block 122 for receiving arms 156.

As described above, longitudinal movement of spring block 122 may change a flexibility of shaft 12. Proximal movement of spring block 122 may decrease a force on the Bowden sheaths, increasing flexibility. Distal movement of spring block 122 may increase a force on the Bowden sheaths, decreasing flexibility.

Figure 3F:
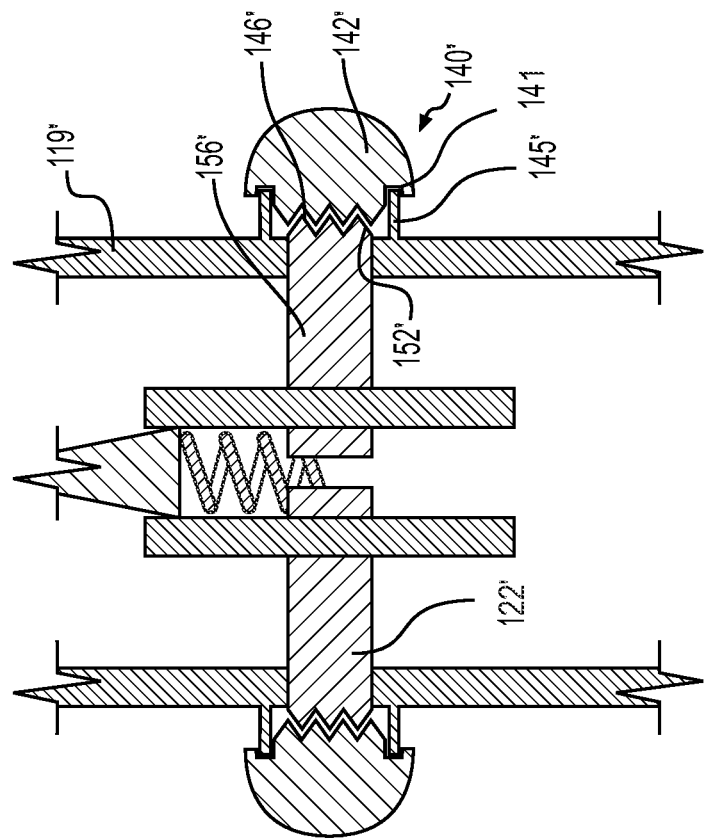
Figure 3E:
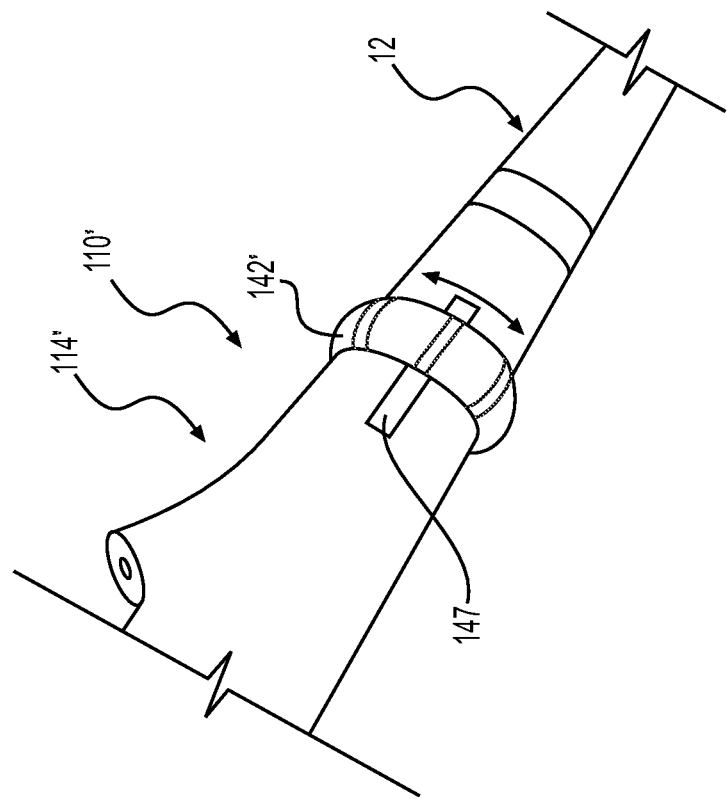

FIGS. 3E and 3F depict an exemplary adjustment mechanism 140', which may have any of the properties of adjustment mechanism 140, except where specified herein. Features of adjustment mechanisms 140, 140' may be combined or used alternatively to one another. As shown in FIG. 3F, adjustment mechanism 140' may have a wheel 142', having any of the properties of wheel 142, except as specified herein. Adjustment mechanism 140 may also include a spring block 122', having any of the properties of spring block 122, except as specified herein. Spring block 122' may have arms 156', which may have any of the properties of arms 156, except as described herein.

Whereas wheel 142 of adjustment mechanism 140 (FIGS. 3A-3D) may extend through slots 147 (FIG. 3E) in housing 119, arms 156' of adjustment mechanism 140' may extend through an opening in a housing 119', which may have any of the properties of housing 119, except as specified herein. Housing 119' may include two slots 147, although only one is visible in the view of FIG. 3E. Another slot 147 (in addition to the slot 147 visible in FIG. 3E) may be disposed diametrically opposite of the slot 147 shown in FIG. 3E. Threads 152' (having any of the properties of threads 152) of arms 156' may engage with threads 146' (having any of the properties of threads 146) of wheel 142'.

Wheel 142' may be inhibited from moving longitudinally (proximally or distally) relative to housing 119' by protrusions 145', which may extend radially outward from an outer surface of housing 119' into complementary recesses 141 of wheel 142'. During rotational movement of wheel 142', which may be caused by a hand of a user, threads 146' may interact with threads 152'. Spring block 122' may be inhibited from rotational movement by guide rails 170a, 170b, 170c, and 170d, as described above with respect to FIGS. 3A-3D. A shape of slots 147 may further limit rotation of arms 156' (and a remainder of spring block 122'). Alternatively, guide rails 170a, 170b, 170c, and 170d may be omitted. Thus, as wheel 142' rotates, spring block 122' may move longitudinally proximally or distally. Arms 156' may travel along slots 147.

FIGS. 4A and 4B depict aspects of another adjustment mechanism 240 for use with a duodenoscope 210, which may have any of the properties of other duodenoscopes described herein. Adjustment mechanism 240 may function like rack and pinion gears in order to translate or otherwise move a spring block 222 proximally and distally. FIG. 4A shows a cross-sectional view along a longitudinal plane of a handle 214. FIG. 4B shows a perspective view of a portion of handle 214. Except as specified herein, handle 214 may have any of the properties of other handles described herein.

As shown in FIGS. 4A and 4B, adjustment mechanism 240 may include a rotatable wheel 242. Wheel 242 may extend through an opening in a wall of a housing 219 of handle 14. An opening that receives wheel 242 may resemble a longitudinal slot in housing 219. Housing 219 may have any of the features of the other housings described herein. One side of wheel 242 may be external to housing 219, such that it is able to be contacted by a hand of a user. Another side of wheel 242 may be inside of housing 219. Wheel 242 may have a rotation axis such that wheel 242 is rotatable in proximal and distal directions. A rotation axis of wheel 242 may be approximately perpendicular to a longitudinal axis of handle 214. An outer surface of housing 219 may include ramps 244 or similar features to assist in positioning a finger of a user in order to rotate wheel 242.

Wheel 242 may have teeth around at least a portion of a circumference thereof. Teeth 246 may function as gear teeth and may also function as gripping aids for a user's finger. FIG. 4A shows teeth 246 as having uniform size, but a size of teeth 246 may be variable. For example, one or more of teeth 246 may be longer and therefore act as a stop to inhibit further rotation of wheel 242.

Spring block 222 may have any of the features of spring block 22 and/or of spring block 122. Spring block 222 may exert a distal force on Bowden sheaths 34a, 34b, as described above, with respect to spring block 22.

A body 250 may extend radially outward from at least a side of spring block 222. Body 250 may be fixed relative to a remainder of spring block 222 and may be rigid. Body 250 may be formed as a single structure with spring block 222 (e.g., formed of a single, uniform material) or may be a separate piece from a remainder of spring block 222. At least a portion of a radially outward surface 252 of body 250 may include teeth 254. Radially outward surface 252 may extend at least approximately parallel to a central longitudinal axis of handle 214. Body 250 may function like a pinion gear.

When a user exerts a proximal force on wheel 242, teeth 246 of wheel 242 may interact with teeth 254 of body 250 in order to move body 250 and a remainder of spring block 222 distally. Distal movement of spring block 222 may exert an increased distal force on Bowden sheaths 234a and 234b (and other Bowden sheaths that may not be shown in the cross-section of FIG. 4A). The increased distal force on Bowden sheaths 234a and 234b (and other Bowden sheaths) may cause shaft 12 (not shown in FIGS. 4A and 4B) to have an increased stiffness.

When a user exerts a distal force on wheel 242, teeth 246 of wheel 242 may interact with teeth 254 of body 250 in order to move body 250 and a remainder of spring block 222 proximally. Proximal movement of spring block 222 may result in a decreased distal force on Bowden sheaths 234a and 234b (and other Bowden sheaths that may not be shown in the cross-section of FIG. 4A) from spring block 222. The decreased distal force on Bowden sheaths 234a and 234b (and other Bowden sheaths) may cause shaft 12 (not shown in FIGS. 4A and 4B) to have a decreased stiffness/increased flexibility.

A size of wheel 242/toothed portion of body 250 and a number and size of threads 246, 254 may be chosen to provide a desired amount, and degree of control (e.g., fine) of proximal and/or distal movement of spring block 222. Wheel 242 and/or housing 119 may include index markers to indicate how far wheel 242 has been rotated and to thus indicate an amount of longitudinal movement of spring block 222.

FIGS. 5A and 5B depict another exemplary adjustment mechanism 340. In order to ease illustration of the relevant features, certain features of a handle 314 (e.g., Bowden cables, Bowden sheaths, elevator wire, etc.) may not be depicted. These features may be present and may have any of the features of the examples described above. FIGS. 5A and 5B depict a cross-section along a longitudinal plane of handle 314. In FIG. 5A, handle 314 is in a first configuration such that shaft 12 (not shown in FIGS. 5A and 5B) has a stiffer configuration. In FIG. 5B, handle 314 is in a second configuration, such that shaft 12 has a less stiff configuration.

Adjustment mechanism 340 may include a lever arm 342. One end of lever 342 may be outside of a housing 319 and may include a ball 344 or other structure to ease use by an operator. Lever arm 342 may extend through an opening of housing 319 so that another end of lever arm 342 is within housing 319. For example, housing 319 may include a longitudinal slot (not shown in the cross-sections of FIGS. 5A and 5B), along which lever arm 342 may move. Lever arm 342 may be rotatable about an axle 346. Axle 346 may be disposed within, and fixed to, housing 319. Housing 319 may include multiple notches 348a, 348b, 348c, 348d for serving as stops for lever arm 342. For example, lever arm 342 may be moved proximally or distally along the channel and then moved laterally into one of notches 348a, 348b, 348c, 348. Therefore, notches 348a, 348b, 348c may provide predetermined positions of lever arm 342, and therefore predetermined stiffness of shaft 12. In FIG. 5A, lever arm may be positioned within notch 348a. In FIG. 5B, lever arm may be positioned within notch 348c.

Lever arm 342 may be hingedly connected to a cam 350. Cam 350 may include a cam arm 352 and a cam body 354. Cam arm 352 may extend outwardly from cam body 354. Lever arm 342 may be hingedly connected to a free end of cam arm 352. Cam body 354 may have an oblong shape, such that cam body 354 has a major axis C of a certain dimension and a minor axis D of a smaller dimension. Cam body 354 may have, for example, an ovoid shape, an oval shape, or an irregular shape.

Movement of lever arm 342 may cause corresponding movement of cam body 354. Cam body 354 may cause a spring block 322 to move proximally or distally. Spring block 322 may have properties of any of the other spring blocks disclosed herein. For example, as shown in FIG. 5A, in a first configuration, cam body 354 may extend between spring block 322 and a fixed leverage portion 360 (e.g., a block, ledge, or other type of body). Leverage portion 360 may be fixed relative to housing 319. Leverage portion 360 may be distal to spring block 322 and may include openings formed therein for Bowden sheaths and/or cables, elevator wires, or other components to pass through.

In the first configuration of FIG. 5A, an angle of cam body 354 may be such that portions of cam body 354 near major axis C contact spring block 322 and leverage portion 360. Major axis C may be relatively more parallel to the longitudinal axis of handle 314, and minor axis D may be relatively more transverse to the longitudinal axis of handle 314 than in the second configuration. In other words, cam body 354 may be more upright between spring block 322 and leverage portion 360, causing block 322 to separate further from leverage portion 360.

In the second configuration of FIG. 5B, an angle of cam body 354 may be such that portions of cam body 354 near minor axis D may contact spring block 322 and leverage portion 360. Minor axis D may be relatively more parallel to the longitudinal axis of handle 314, and major axis C may be relatively more transverse to the longitudinal axis of handle 314 than in the first configuration. In other words, cam body 354 may be flatter between spring block 322 and leverage portion 360, allowing spring block 322 to move relatively closer to leverage portion 360. Shapes of cam body 354 and leverage portion 360 may be such that force is distributed across cam body 354, including portions of cam body 354 closer to arm 352.

Comparing the first configuration of FIG. 5A with the second configuration of FIG. 5B, spring block 322 may be relatively more distal in the second configuration than in the first configuration. Thus, as explained above, spring block 322 may exert a larger force on Bowden sheaths in the second configuration than in the first configuration. Therefore, shaft 12 may be stiffer in the second configuration than in the first configuration. Moving lever arm 342 proximally may cause cam body 354 to become increasingly upright and may cause shaft 12 to become increasingly flexible due to proximal movement of spring block 322. Moving lever arm 342 distally may cause cam body 354 to become increasingly flat and may cause shaft 12 to become increasingly stiff due to a distal movement of spring block 322.

Figure 6D:
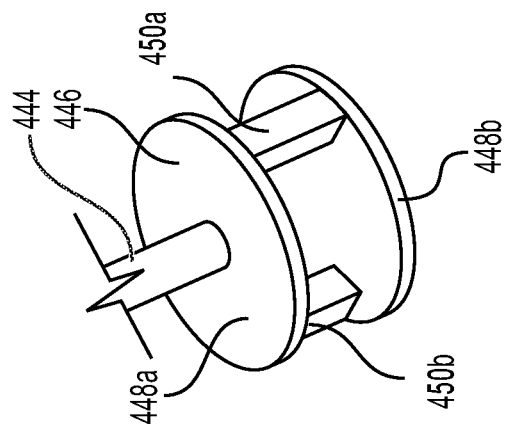
Figure 6C:
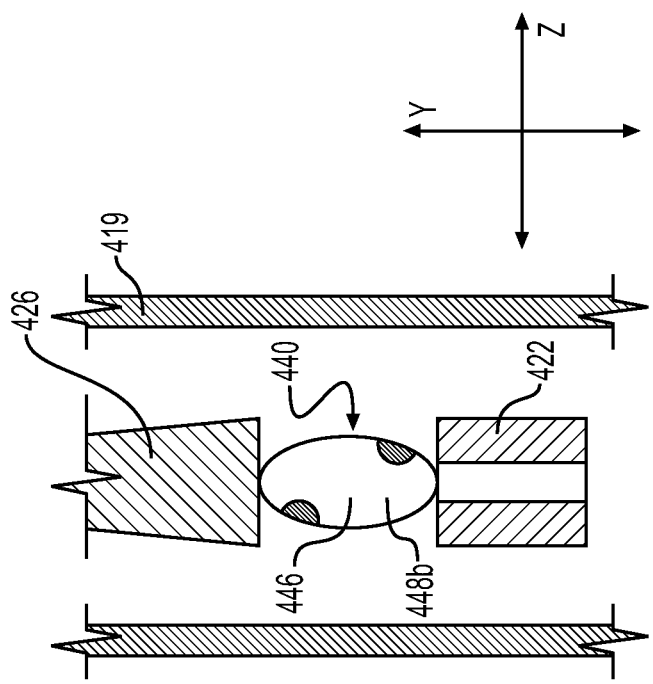
Figure 6F:
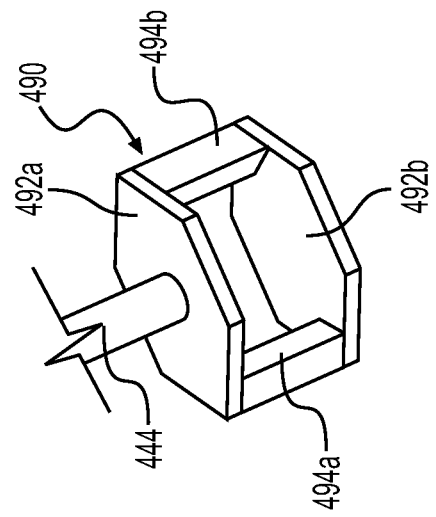
Figure 6E:
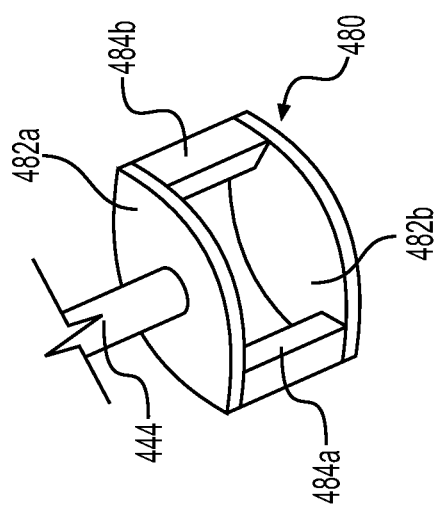

FIGS. 6A-6F depict an alternative adjustment mechanism 440. FIG. 6A depicts a first cross-sectional view of adjustment mechanism 440 in a first configuration, and FIGS. 6B and 6C depict a second cross-sectional view of adjustment mechanism 440, with adjustment mechanism 440 in the first configuration (FIG. 6B) and a second configuration (FIG. 6C). The views of FIGS. 6B and 6C may be rotated by ninety degrees with respect to FIG. 6A, as shown by the coordinate systems of the figures. FIGS. 6D-6F depict perspective views of exemplary cams for use with adjustment mechanism 440. Elements such as Bowden cables, Bowden sheaths, the spring, and the elevator control wire are not shown in FIGS. 6A-6C for ease of illustration of adjustment mechanism 440. Those elements, as shown in FIGS. 2A and 2B and other figures, may have any of the properties described with respect to those figures.

As shown in FIG. 6A, a rotatable knob 442 may rotate about an axle 444 in the direction shown by the arrow. Axle 444 may extend in a radial direction, perpendicular to a longitudinal axis of a handle 414, through an opening in housing 419. Handle 414 may have properties of any of the handles described herein. Axle 444 may be connected at a radially outward end to rotatable knob 442. A radially inner end of axle 444 may be fixed to a surface of a cam 446.

FIGS. 6A-6D depict different views of cam 446. Cam 446 may include two bases 448a, 448b. Axle 444 may be fixed to an outer surface of base 448*a*. Two supports 450*a*, 450*b* may extend between bases 448*a* and 448*b*. As shown in FIGS. 6B-6D, bases 448*a* and 448*b* may have an oval shape. Supports 450*a*, 450*b* may be disposed diagonally from one another, in an area where a short side of base 448*a*/448*b* transitions into a long side of base 448*a*/448*b*. A central part of cam 446 may be open between bases 448*a*, 448*b* to allow passage of components such as Bowden cables and the elevator wire.

As shown in FIGS. 6A and 6B, in a first configuration, cam 446 may be positioned such that a minor axis of cam 446 is approximately parallel to a longitudinal axis of handle 414. In other words, longer sides of cam 446 may contact a spring block 422 (which may have any of the properties of the other spring blocks disclosed herein) and a body 426 (which may have any of the properties of the other bodies disclosed herein).

Knob 442 may be rotated in order to rotate cam 446 by a corresponding amount. For example, knob 442 may be rotated by ninety degrees in order to transition adjustment mechanism 440 to a second configuration, shown in FIG. 6C. In the second configuration, cam 446 may be positioned such that a major axis of cam 446 is approximately parallel to a longitudinal axis of handle 414. In other words, shorter sides of cam 446 may contact spring block 422 and body 426.

Due to the difference in orientation of cam 446, spring block 422 may be positioned relatively more distally in the second configuration (FIG. 6C) than in the first configuration (FIGS. 6A and 6B). In the second configuration (FIG. 6C), a distal force on Bowden sheaths (not shown) may be greater than in the first configuration. Therefore, shaft 12 (see, e.g., FIGS. 1A-2B) may be stiffer in the second configuration.

Adjustment mechanism 440 may also have variable configurations between the first configuration and the second configuration, to allow for fine adjustment and variable stiffness of shaft 12. Knob 442 may offer tactile feedback to a user about a position of knob 442 and a stiffness of shaft 12. Visual indicators on knob 442 and/or housing 419 may alternatively or additionally indicate a position of knob 442 and a corresponding position of cam 446 (and a corresponding stiffness of shaft 12).

As shown in FIGS. 6E and 6F, an oval shape of bases 448*a* and 448*b* of cam 446 is merely exemplary. For example, a cam 480 (FIG. 6E) may be used in place of cam 446. Cam 480 may have any of the properties of cam 446 except as described below. Cam 480 may have bases 482*a*, 482*b*. Bases 482*a*, 482*b* may have an approximately diamond shape, with at least some corners of the diamond shape being rounded. For example, as shown in FIG. 6E, a major axis of cam 480 may terminate in pointed corners, while a minor axis of cam 480 may terminate in rounded corners. Supports 484*a*, 484*b* may connect base 482*a* to base 482*b*. Supports 484*a* and 484*b* may be positioned proximate to a pointed corner of cam 480, on opposite sides so that they are diagonal from one another. A position of supports 484*a*, 484*b* may facilitate passage of elements such as Bowden cables and the elevator wire between bases 482*a* and 482*b*. Supports 484*a* and 484*b* may alternatively have other positions on cam 480.

FIG. 6F depicts an alternative example cam 490, which may be used in place of cam 446 and may have any of the properties of cams 446, 480. Cam 489 may have bases 492*a*, 492*b*. Bases 492*a*, 492*b* may have an elongated hexagon shape. Supports 494*a*, 494*b* may connect base 492*a* to base 492*b*. Supports 494*a* and 494*b* may be positioned proximate to a pointed end of cam 490, on opposite sides from one another so that they are diagonal from one another. A position of supports 494*a*, 494*b* may facilitate passage of elements such as Bowden cables and the elevator wire between bases 492*a* and 492*b*. Supports 494*a* and 494*b* may alternatively have other positions on cam 480. The corners of cam 490 may provide feedback to a user about a position of cam 490 and a stiffness of shaft 12. For example, as one of the corners contacts spring block 422 or body 426, it may provide tactile feedback of, for example, preset resting points of cam 490. Other shapes of cams may be used, in addition to those described above.

FIGS. 7A and 7B depict a further exemplary adjustment mechanism 540. FIG. 7A depicts a cross-sectional view of handle 514 along a longitudinal plane of handle 514. FIG. 7B depicts a proximally-facing cross section of handle 514. The coordinates systems of FIGS. 7A and 7B show relationships between the views of FIGS. 7A and 7B.

A slide lever 542 may be disposed on an outer surface of a housing 519 of handle 514. Housing 519 and handle 514 may have any of the properties of other housings and handles, respectively, disclosed herein, except where specified. Slide lever 542 may be pivotally connected, via an axle 546, to an arm 544 that extends proximally and radially inward from a proximal portion of slide lever 542. A portion of slide lever 542 and/or arm 544 may extend through an opening in a wall of housing 519.

An end of arm 544, opposite to an end of arm 544 that is connected to slide lever 542, may be fixed to a spring block 522, which may have any of the features of other spring blocks disclosed herein. Alternatively, arm 544 may not be fixed to spring block 522 but may otherwise exert forces on spring block 522, as described below. As shown in FIG. 7B, arm 544 may be attached to a central portion of a distally-facing surface of spring block 522, such that arm 544 does not interfere with Bowden cables 532*a*, 532*b*, 532*c*, 532*d* (which may have any of the properties of Bowden cables 132*a*, 132*b*) or elevator control wire 536 (which may have any of the properties of elevator control wire 36). Bowden cables 532*a*, 532*b*, 532*c*, 532*d* may extend longitudinally through lumens of spring block 522 having proximal and distal openings. Elevator control wire 536 may rest in a recess that extends longitudinally from a proximal end of spring block 522 to a distal end of spring block 522.

As shown in FIG. 7A, slide lever 542 may include a contact portion 548 for being contacted by a user, and an arm 550 that extends proximally along a longitudinal axis of handle 514 from contact portion 548. Arm 550 may include a protrusion 552 extending radially inward from arm 550. Housing 519 may include a plurality of openings or recesses 554*a*, 554*b*, 554*c*, 554*d*, for receiving protrusion 552. In FIG. 7A, protrusion 552 may be received within recess 554*a*. Therefore, slide lever 542 may be fixed relative to housing 519.

In order to move slide lever 542 proximally or distally, a user may press radially inward on contact portion 548 in order to rotate slide lever 542 about axis 546. Such rotation may cause arm 550 to move radially outward from an outer surface of housing 519, removing protrusion 552 from one of recesses 554*a*, 554*b*, 554*c*, 554*d*. While contact portion 548 is depressed, the user may move slide lever 542 proximally or distally, due to the force provided by a spring (not shown in FIGS. 7A and 7B). A user may release contact portion 548 in order to position protrusion 552 within another of recesses 554*a*, 554*b*, 554*c*, 554*d*. Slide lever 542 may be limited from moving proximally or distally by an interaction between protrusion 552 and one of recesses 554a, 554b, 554c, 554d.

In embodiments, when slide lever 542 is moved proximally, spring block 522 may be moved proximally. When slide level 542 is moved distally, spring block 522 may move distally. A guide 570 may extend around at least a portion of spring block 522 to limit movement of spring block 522 to longitudinal movement, instead of radial/lateral movement. As shown in FIG. 7B, guide 570 may surround three sides of spring block 522. The three surrounded sides may exclude a side of spring block 522 that has a groove for receiving elevator control wire 536. Guide 570 may be fixed to housing 519 or to another component fixed to housing 519. Alternatively, guide 570 may be integrally formed with housing 519.

Where arm 544 is not fixed to spring block 522, proximal movement of slide lever 542 may cause arm 544 to press against spring block 522, thereby pushing spring block 522 proximally. Distal movement of slide lever 542 may allow a spring (having properties of any of the springs disclosed herein) to press spring block 522 distally until it encounters arm 544.

As spring block 522 moves proximally, a force on Bowden sheaths (not shown in FIGS. 7A and 7B) may be smaller, and a flexibility of shaft 12 (not shown in FIGS. 7A and 7B) may increase, as described above with respect to other adjustment mechanisms. As spring block 522 moves distally, a force on the Bowden sheaths may be greater, and shaft 12 may be stiffer, as described above with respect to other adjustment mechanisms.

FIGS. 8A and 8B show another exemplary adjustment mechanism 640. FIGS. 8A and 8B show cross-sectional views along a longitudinal plane of a handle 614. FIG. 8A shows adjustment mechanism 640 in a first configuration, and FIG. 8B shows adjustment mechanism 640 in a second configuration. Adjustment mechanism 640 may include a scissor lift. Handle 614 may have any of the properties of the other handles described herein, except where specified below. For ease of illustrating adjustment mechanism 640, components of handle 614, such as Bowden cables, Bowden sheaths, the elevator control wire, and the spring may be omitted. It will be appreciated that elements of, for example, handle 14 may be incorporated into handle 614.

As shown in FIGS. 8A and 8B, an actuator 642 may be movable in a radially inward and outward direction, as shown by the arrows in FIGS. 8A and 8B. Actuator 642 may have a shaft 644. One end of shaft 644 may be interact with one or more of a pair of scissor arms 646, 648. Scissor arms 646, 648 may be rotatably connected to one another via an axle 650. Scissor arms 646 and shaft 644 may be offset from a central longitudinal axis and/or have openings to allow for passage of components such as Bowden cables, Bowden sheaths, or elevator wires.

In the first configuration of FIG. 8A, scissor arms 646, 648 may be in a relatively open configuration. In the second configuration of FIG. 8B, scissor arms 646, 648 may be in a relatively closed configuration. In transitioning from the first configuration to the second configuration, proximal ends of scissor arms 646, 648 may move radially inward and proximally, to the second configuration of FIG. 8B. Distal ends of scissor arms 646, 648 may leverage off of body 647, which may be fixed relative to a housing of handle 614. For example, body 647 may be integrally formed with the housing.

The proximal movement of the proximal ends of scissor arms 646, 648 may exert a proximally-directed force on a spring block 622, which may have any of the properties of any of the spring blocks disclosed herein. Scissor arms 646, 648 may rest against a distally-facing surface of spring block 622. Additionally or alternatively, a groove or other feature of spring block 622 may receive one or more of scissor arms 646, 648. The proximal ends of scissor arms 646, 648 may ride in the groove as the adjustment mechanism transitions from the first configuration to the second configuration.

As scissor arms 646, 648 close (move from the first configuration of FIG. 8A to the second configuration of FIG. 8B), proximal movement of the proximal ends of scissor arms 646, 648 may push spring block 622 proximally. Where the proximal ends are retained by or within spring block 622, distal movement of the proximal ends may pull spring block 622 distally. Additionally or alternatively, distal movement of the proximal ends of scissor arms 646, 648 may permit a spring (not shown and having any properties of the springs disclosed herein, such as spring 24) to exert a distal force on spring block 622, pushing spring block 622 distally.

Proximal movement of spring block 622 may cause spring block 622 to exert less force on the Bowden sheaths (not shown) of handle 614, as described above, thereby causing shaft 12 (not shown in FIGS. 8A and 8B) to become more flexible. Distal movement of spring block 622 may cause spring block 622 to exert a greater force on the Bowden sheaths of handle 614, as described above, thereby causing shaft 12 to become stiffer/less flexible.

In one example, at least a radially inward portion of shaft 644 may include threads. Shaft 644 may pass through openings in distal portions of scissor arms 646, 648. Actuator 642 may function as a rotatable knob that causes shaft 644 to rotate. As shaft 644 rotates in one direction, it may cause scissor arms 646, 648 to open and to transition from the first configuration to the second configuration. As shaft 644 rotates in the other, opposite direction, it may cause scissor arms 646, 648 to close and transition from the second configuration to the first configuration.

The openings in scissor arms 646, 648 may be threaded or may be sufficiently thin that inner surfaces of the openings interact with the threads of shaft 644. Threads in a portion of shaft 644 that interacts with first scissor arm 646 may face a first direction, and threads in a second portion of shaft 644 that interacts with second scissor arm 648 may face a second, opposite direction. Thus, the threads of shaft 644 may cause scissor arms 646 to open and/or close, moving in radially opposite directions from one another.

In an alternative, shaft 644 may be hingedly connected to a proximal end of first scissor arm 646 of the pair of scissor arms 646, 648. Actuator 642 may include a push button. As actuator 642 is depressed, shaft 644 may exert a radially inward force on a distal end of first scissor arm 646. The radially inward force may cause first scissor arm 646 to rotate such that a length of first scissor arm extends further along a longitudinal axis of handle than before button 642 was depressed. A proximal end of first scissor arm 646 may move radially inward and proximally, to the second configuration of FIG. 8B.

A mechanism of adjustment mechanism 640 may cause second scissor arm 648 to move in conjunction with first scissor arm 646, in a mirror image of first scissor arm 646. For example, a groove of spring block 622 receiving proximal ends of scissor arms 646, 648 may retain the proximal ends and cause a proximal end of second scissor arm 648 to move proximally and radially inward, along with the proximal end of first scissor arm 646. Additionally or alternatively, axle 650 may be configured such that first and second scissor arms 646, 648 are not independently movable. Thus, movement of first scissor arm 646 caused by shaft 644 may cause second scissor arm 648 to move in a corresponding manner.

Button 642 may be pulled radially outward in order to transition the adjustment mechanism to the first configuration, opening scissor arms 646, 648, and causing the proximal ends of scissor arms 646, 648 to move distally and outwardly.

FIGS. 9A and 9B show aspects of an additional adjustment mechanism 740. FIG. 9A shows a perspective view of a handle 714, and FIG. 9B shows a perspective view of a camming mechanism 750. Camming mechanism 750 may be combined with any of the aspects described above, including for example, those of FIGS. 5A-6F.

As shown in FIG. 9A, a lever 742 may extend radially outward from a surface of a housing 719 (which may have properties of any of the other housings described herein). A radially outward end of lever 742 may terminate in a ball 744 or another structure for facilitating grip of a user and manipulation of lever 742. Lever 742 may extend through a slot 746 in housing 719. Slot 746 may extend in a circumferential direction of housing 719, (transverse to a longitudinal axis of housing 719), such that lever 742 is movable within slot 746.

A radially inner end of lever 742 may be fixed to a cam 748. Cam 748 may have a round perimeter. Cam 748 may resemble a washer with a camming ramp 750 extending from a face of the washer. Camming ramp 750 may extend around some or all of a perimeter/circumference of cam 748. Cam 748 may include a central opening 752, which may receive an axle allowing for rotation of cam 748 about the axle.

Moving lever 742 within slot 746 may cause rotation of cam 748 about a central axis of cam 748 (where opening 752 is located). As depicted in FIG. 9A, if cam 748 has the orientation shown in FIG. 9B, movement of lever 942 to the left may engage camming ramp 750 and movement of lever 742 to the right may disengage camming ramp 750. As camming ramp 750 is engaged, camming ramp 750 may exert a progressively greater force on an element of handle 714, against the force of a spring (not shown). For example, camming ramp 750 may exert a progressively increasing proximal force on an element of handle 714 as the cam 748 rotates in a clockwise direction. If lever 742 is moved to the right, cam 748 may be rotated in a counter-clockwise direction to disengage camming ramp 750 and remove or decrease a proximal force exerted by camming ramp 750.

Camming ramp 750 may directly engage a spring block (not shown but having properties of other spring blocks disclosed herein) or may exert a force on a structure that, in turn, exerts a force on the spring block. For example, the cam 748 may be mounted distally of the spring block, on a portion of housing 719 receiving the spring block, or on a body separate from housing 719 but fixed relative to housing 719. For example, the spring block may include arms like arms 156 (FIGS. 3A-3C) or like body 250, which may engage with camming ramp 750. Movement of the spring block due to interactions with camming ramp 750 may result in stiffening or increased flexibility of shaft 12 (not depicted in FIGS. 9A and 9B), according to the mechanisms described above.

Cam 748 may have alternative orientations within handle 714 to allow forces to be exerted by camming ramp 750 in varying directions in order to facilitate stiffening/relaxing of shaft 12 (not depicted in FIGS. 9A and 9B).

Figures 10A, 10B:
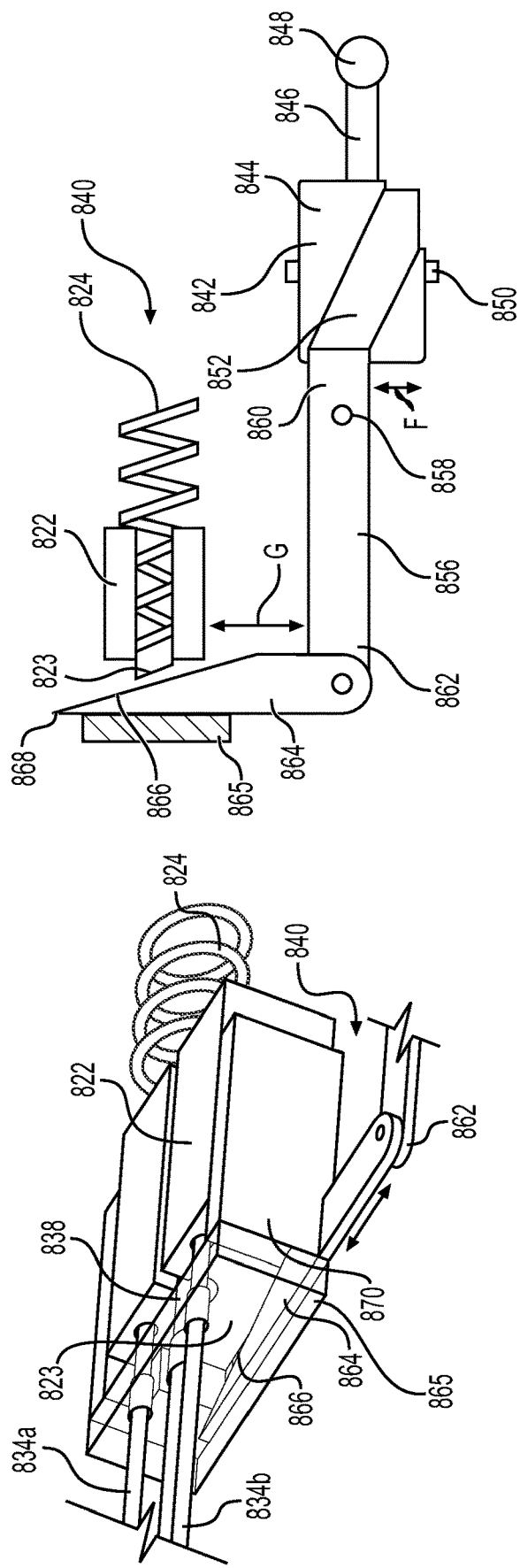
Figure 10D:
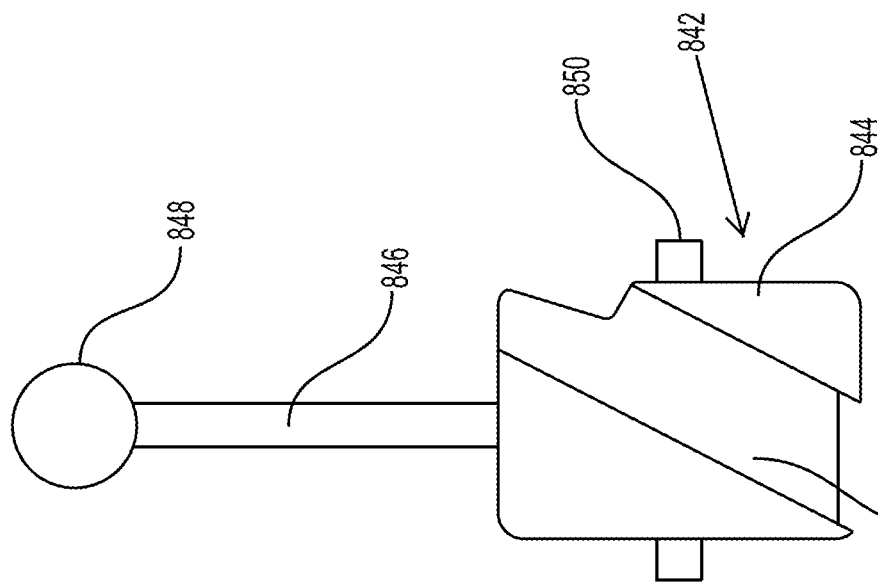
Figure 10C:
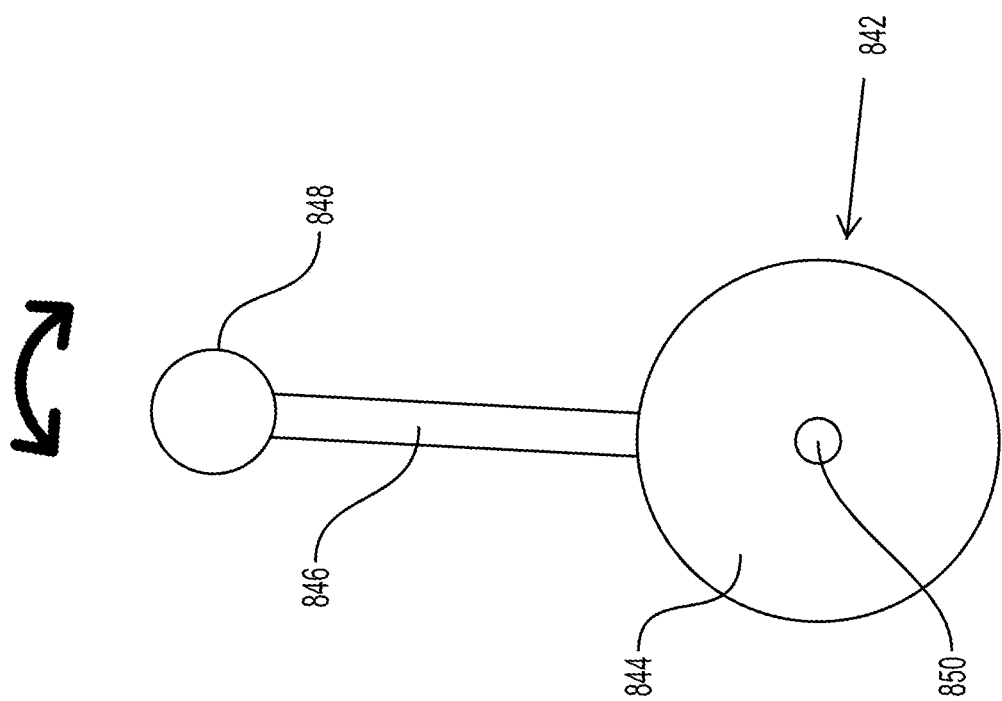

FIGS. 10A-10D depict views of aspects of an exemplary adjustment mechanism 840. FIG. 10A depicts a perspective view looking proximally and radially inward at aspects of adjustment mechanism 840. FIG. 10B depicts a side view of aspects of adjustment mechanism 840. FIGS. 10C and 10D are side views of a lever 842 of adjustment mechanism 840.

FIGS. 10A and 10B depict elements of adjustment mechanism 840. Adjustment mechanism 840 may include lever 842. Lever 842 may include a spool 844 and an arm 846 extending radially outward from spool 844. An end of arm 846 may terminate in a ball 848 or other structure to facilitate gripping and manipulation by an operator. Spool 844 may be rotatable about an axle 850, as shown by the arrow in FIG. 10C. Spool 844 may include a helical groove 852 that extends at least partially around an outer circumference of spool 844. Groove 852 may be sized so as to receive a proximal end of a linkage arm 856, described in further detail below. Groove 852 may extend from one face of spool 844 to another face of spool 844.

Adjustment mechanism 840 may also include linkage arm 856, which may be rotatable about an axle 858. A proximal end 860 of linkage arm 856 may be received within groove 852, such that groove 852 is slidable with respect to linkage arm 856 (linkage arm 856 slides in groove 852) but proximal end 860 does not disengage from groove 852 (e.g., fall out a distal end of groove 852). Rotation of lever 842 and spool 844 may cause linkage arm 856 to rotate about axle 858. Proximal end 860 may move radially inward and outward as a result (as shown by arrow F), perpendicularly to a longitudinal axis of linkage arm 856. A distal end of linkage arm 856 may also move radially inward and outward, perpendicularly to the longitudinal axis of linkage arm 856. Because axle 858 may be closer to proximal end 860 than to a distal end 862 of linkage arm 856, proximal end 860 may move less in a radial direction than distal end 862 of linkage arm 856.

For example, from the configuration of FIG. 10B, lever arm 846 may be rotated in a direction out of the page, thereby rotating spool 844. As spool 844 rotates, proximal end 860 may slide along groove 852. A portion of groove 852 contacting proximal end 860 may be a portion that progressively extends further radially outward, causing proximal end 860 to move radially outward. The rotation may cause distal end 862 of linkage arm 856 to move radially inward, toward a spring block 822, described in further detail below.

Distal end 862 of linkage arm 856 may be hingedly connected to a ramp arm 864. Movement of distal end 862 radially inward and outward may cause ramp arm 864 to move radially inward and outward, respectively, along a longitudinal axis of ramp arm 864, as shown by arrow G. Ramp arm 864 may move linearly, along a longitudinal axis of ramp arm 864, rather than rotating, because movement of ramp arm 864 along a longitudinal axis of a handle (and along a longitudinal axis of Bowden sheaths 834a, 834b, described in further detail below), because such movement of 864 may be restricted by a structure. For example, a support 870 may be fixed relative to a housing (not shown) of a handle including elements of adjustment mechanism 840. Support 870 may include at least one wall extending along the longitudinal axis of the handle. Ramp arm 864 may pass through a slot or other opening of the wall of support 870, which may restrict movement of ramp arm 864 to a direction approximately along a longitudinal axis of ramp arm 864.

Ramp arm 864 may be thin such that it is approximately flat in one dimension. Ramp arm 864 may include a tapered surface 866 such that a width of ramp arm 864 gradually increases from an end 868 of ramp arm 864 that is farthest from linkage arm 856 in a direction toward linkage arm 856. End 868 of ramp arm 864 may be pointed. Tapered surface 866 may be straight or curved.

As shown in FIGS. 10A and 10B, distal surface 823 of a spring block 822 may abut tapered surface 866. Spring block 822 may have any of the properties of other spring blocks described herein. Distal surface 823 may exert a distal force on Bowden sheaths 834a, 834b (and/or other Bowden sheaths that are not visible in FIG. 10A). Distal surface 823 may include a tapered portion that may have a shape complementary to a surface of ramp arm 864. Spring 824 may exert a distal force on spring block 822 and may have any of the properties of other the springs described herein. Because ramp arm 864 is thin/approximately flat, it may not interfere with Bowden sheaths 834a, 834b, or a hypotube 836 housing an elevator control wire (which may have any of the properties of the other elevator wires described herein).

As ramp arm 864 moves radially inward (in an upward direction of FIG. 10B), tapered surface of 866 may push spring block 822 progressively proximally. As ramp arm 864 moves radially outward (in a downward direction of FIG. 10B), spring 824 (or another mechanism) may push spring block 822 progressively distally as a width of ramp arm 864 grows smaller. As spring block 822 moves distally, it may exert a greater force on Bowden sheaths 834a, 834b (and/or other Bowden sheaths that are not visible in FIG. 10A), causing a shaft 12 (not depicted in FIGS. 10A-10D) to become stiffer/less flexible. As spring block 822 moves proximally, it may exert a smaller force on Bowden sheaths 834a, 834b (and/or other Bowden sheaths that are not visible in FIG. 10A), causing a shaft 12 (not depicted in FIGS. 10A-10D) to be less stiff/more flexible.

Properties of ramp arm 864, including tapered surface 866, may be chosen to allow for fine adjustment and to set limits on the amount spring block 822 may move and thickness may thereby be adjusted. A maximum width of ramp arm 864 may determine a maximum amount that spring block 822 may be moved proximally or distally.

In use, an operator may insert shaft 12 into a body lumen of a subject. The operator may utilize one of the adjustment mechanisms depicted in FIGS. 3A-10D in order to adjust a stiffness of shaft 12. The stiffness may be adjusted one or more times. For example, following removal of the gastric loop discussed with respect to FIGS. 1A and 1B, a stiffness of shaft 12 may be adjusted so that shaft 12 is less flexible to limit undesired movement of shaft 12.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device including:
a shaft configured to be inserted into a body lumen of a subject;
a handle at a proximal end of the shaft, the handle including a slidable lever and an arm extending radially inward into a cavity defined by a housing of the handle, wherein the slidable lever includes a contact portion for being contacted by a user;
at least one Bowden cable having a Bowden sheath; and
a body configured to exert a distal force on a proximal end of the Bowden sheath, wherein the slidable lever is configured to move the body proximally or distally, and wherein the slidable lever is configured to be transitioned from a first, proximal configuration, in which the shaft has a first stiffness, to a second, distal configuration, in which the shaft has a second stiffness, wherein the first stiffness is different from the second stiffness.

2. The medical device of claim 1, wherein the shaft includes at least one control mechanism extending therethrough, and wherein the slidable lever is configured to change a force on the at least one control mechanism.

3. The medical device of claim 2, wherein a first force is exerted on the slidable lever in the first configuration and a second force is exerted on the slidable lever in the second configuration, and wherein the first force is greater than the second force.

4. The medical device of claim 1, wherein the handle includes a plurality of openings or recesses configured to receive a portion of the slidable lever to fix the slidable lever relative to the handle.

5. The medical device of claim 1, wherein the arm of the slidable lever is configured to contact a distally-facing surface of the body.

6. The medical device of claim 1, wherein the slidable lever is pivotally connected to the arm.

7. A medical device including:
a shaft configured to be inserted into a body lumen of a subject; and
a handle at a proximal end of the shaft, the handle including:
at least one Bowden cable having a Bowden sheath;
a body configured to exert a distal force on the Bowden sheath; and
an actuator coupled to a scissor lift, wherein rotation of the actuator in a first direction closes the scissor lift and moves the body proximally, wherein rotation of the actuator in a second direction opens the scissor lift and moves the body distally, and wherein proximal movement and distal movement of the body changes an amount of the distal force on the Bowden sheath.

8. The medical device of claim 7, wherein the actuator includes a knob and a shaft fixed to the scissor lift, wherein the shaft includes threads configured to interact with the scissor lift.

9. The medical device of claim 8, wherein the threads of the shaft include a first portion of threads and a second portion of threads, wherein the first portion of threads interact with a first arm of the scissor lift and the second portion of threads interact with a second arm of the scissor lift.

10. The medical device of claim 9, wherein the first portion of threads faces a first direction, and wherein the second portion of threads faces a second direction.

11. The medical device of claim 7, wherein the scissor lift is configured to contact a distally-facing surface of the body.

12. The medical device of claim 7, wherein the scissor lift includes a first arm hinged relative to a second arm, and wherein, upon closing the scissor lift, proximal ends and distal ends of each of the first arm and the second arm are configured to move inwards and towards one another.

13. A medical method, comprising:
inserting a shaft of a medical device into a body lumen of a subject; and activating an adjustment mechanism on a handle of the medical device in order to cause the shaft of the medical device to increase in flexibility, wherein the adjustment mechanism includes a lever having a contact portion configured for contact by a user, and wherein the lever is configured to pivot.

14. The medical method of claim 13, wherein activating the adjustment mechanism causes a body to move proximally relative to a housing of the handle.

15. The medical method of claim 13, further comprising:
de-activating the adjustment mechanism on the handle of the medical device in order to cause the shaft of the medical device to decrease in flexibility; and
locking the lever relative to the handle.

16. The medical method of claim 15, wherein the medical device further includes a body, and wherein, upon activating the adjustment mechanism of the medical device, the body is moved proximally, and wherein, upon de-activating the adjustment mechanism of the medical device, the body is moved distally.

17. The medical method of claim 13, wherein the lever includes a cam.

18. The medical method of claim 17, wherein the cam is positioned between a body and a structure that is fixed relative to the handle.

19. The medical method of claim 18, wherein the cam is movable via the lever.

20. The medical method of claim 13, wherein the lever includes an arm, and wherein the arm is configured to be received within a plurality of notches disposed on the handle.

\* \* \* \* \*